(12) United States Patent
Garcia et al.

(10) Patent No.: US 9,995,688 B2
(45) Date of Patent: Jun. 12, 2018

(54) USE OF SUPERHYDROPHOBIC SURFACES FOR LIQUID AGGLUTINATION ASSAYS

(75) Inventors: Antonio Garcia, Chandler, AZ (US); John Schneider, Phoenix, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 48 days.

(21) Appl. No.: 13/497,478

(22) PCT Filed: Aug. 17, 2010

(86) PCT No.: PCT/US2010/045692
§ 371 (c)(1),
(2), (4) Date: Jun. 20, 2012

(87) PCT Pub. No.: WO2011/034678
PCT Pub. Date: Mar. 24, 2011

(65) Prior Publication Data
US 2012/0264113 A1     Oct. 18, 2012

Related U.S. Application Data

(60) Provisional application No. 61/244,359, filed on Sep. 21, 2009.

(51) Int. Cl.
*G01N 21/82*   (2006.01)
*G01N 33/543*  (2006.01)
*G01N 33/536*  (2006.01)
*G01N 33/53*   (2006.01)
*G01N 21/49*   (2006.01)
*G01N 21/03*   (2006.01)

(52) U.S. Cl.
CPC ............. *G01N 21/82* (2013.01); *G01N 21/49* (2013.01); *G01N 33/5304* (2013.01); *G01N 33/536* (2013.01); *G01N 33/54346* (2013.01); *G01N 2021/035* (2013.01)

(58) Field of Classification Search
None
See application file for complete search history.

(56) References Cited

U.S. PATENT DOCUMENTS 6,248,597 B1 *   6/2001   Eda et al. ............... 436/518
6,514,770 B1 *   2/2003   Sorin ..................... 436/518
(Continued)

OTHER PUBLICATIONS

Hong, X. et al., "Application of Superhydrophobic surface with high adhesive force in no. lost transport of superparamagneict microdroplet" Journal of the Amercian Chemical Society (2007) 129:1478-1479.*
(Continued)

*Primary Examiner* — Scott Long
*Assistant Examiner* — Gary E Hollinden
(74) *Attorney, Agent, or Firm* — Kramer Amado, PC

(57) ABSTRACT

This invention relates to the use of thermodynamically incompatible surfaces in agglutination assays for the express purpose of using the sample as a key component of the detection instrument. Specifically, the invention relates to formation of a lense and a virtual container for rapid mixing via thermal energy by a sample liquid disposed on a superhydrophobic surfaces, and a subsequent specific analyte or overall protein concentration assay using particles agglutination for use in the industrial, environmental, and clinical laboratory test fields.

31 Claims, 17 Drawing Sheets

(56) References Cited

U.S. PATENT DOCUMENTS

| | | | |
|---|---|---|---|
| 8,895,072 B2* | 11/2014 | Yan et al. | 424/490 |
| 9,110,055 B2* | 8/2015 | Cai | G01N 33/54346 |
| 9,364,830 B2* | 6/2016 | Carbone | B01L 3/5027 |
| 2005/0153460 A1* | 7/2005 | Kawasaki et al. | 436/524 |
| 2006/0089810 A1* | 4/2006 | Matsumoto et al. | 702/19 |
| 2006/0257926 A1* | 11/2006 | Yamazaki et al. | 435/7.1 |
| 2008/0009018 A1* | 1/2008 | Ouyang et al. | 435/7.1 |
| 2009/0297448 A1* | 12/2009 | Yan et al. | 424/9.1 |
| 2010/0285573 A1* | 11/2010 | Leck et al. | 435/288.4 |
| 2012/0058697 A1* | 3/2012 | Strickland et al. | 442/59 |
| 2013/0288254 A1* | 10/2013 | Pollack et al. | 435/6.12 |

OTHER PUBLICATIONS

Sheen, Y-C. et al., "New approach to fabricate an extremely super-amphiphobic surface based on fluorinated silica nanoparticles", Journal of Polymer Science: Part B: Polymer Physics (2008) 46:1984-1990.*

Rastogi, V. et al., "Synthesis of light-diffracting assemblies from microspheres and annoparticles in droplets on a superhydrophobic surface", Advanced Materials (2008) 20:4263-4268.*

* cited by examiner

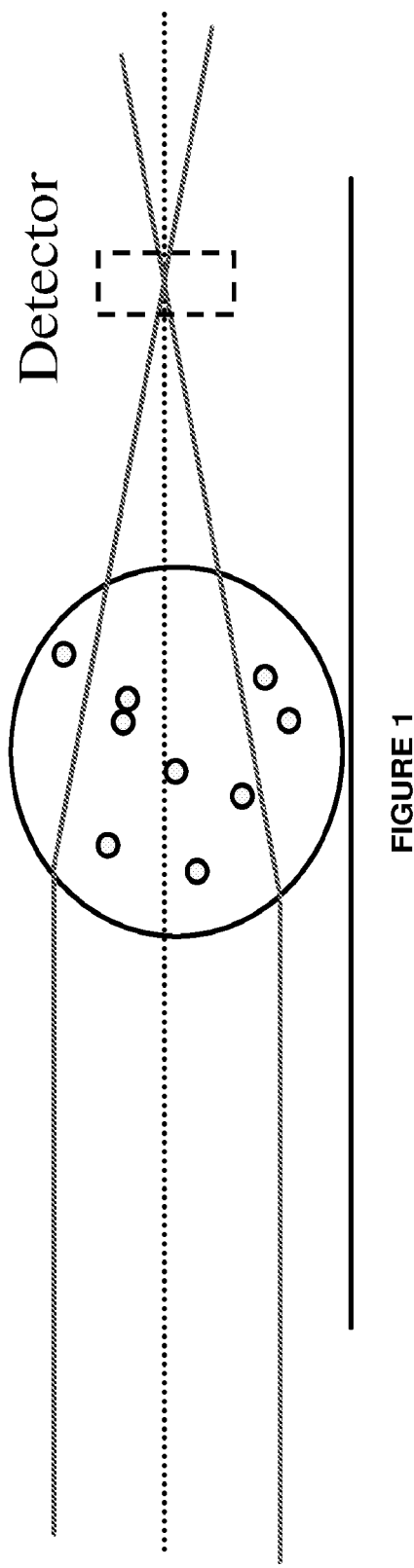

101 Detector
102 Ball Lens
103 Superhydrophobic surface
104 LED
105 Optical Fiber
106 Sample drop
107 Sample Holder (C)
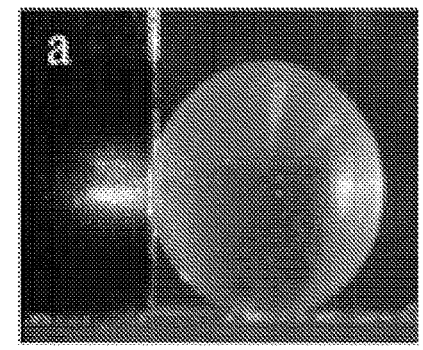
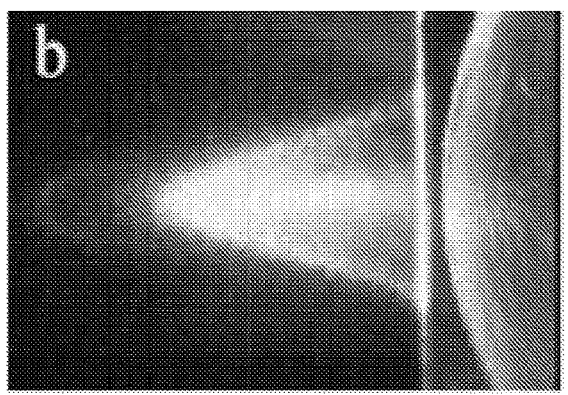
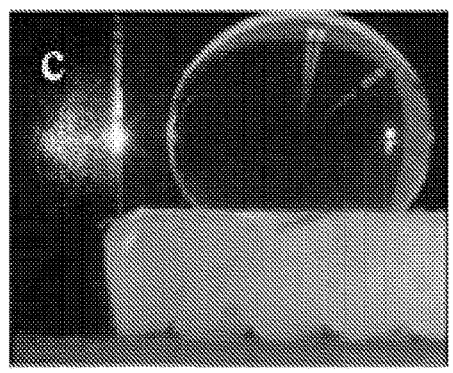
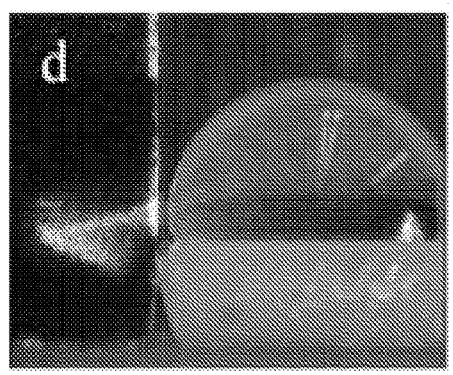
FIGURE 11C

USE OF SUPERHYDROPHOBIC SURFACES FOR LIQUID AGGLUTINATION ASSAYS

FIELD OF INVENTION

The present invention relates to assays for determining a specific analyte or total protein via particle agglutination by focussing light from a drop on a superhydrophobic surface. More particularly, the invention relates to formation of a lense and a virtual container for rapid mixing via thermal energy by a sample liquid disposed on superhydrophobic surfaces, and a subsequent agglutination assay to measure a trace constituent or total protein using agglutination for use in the industrial, environmental, and clinical laboratory test fields.

BACKGROUND OF THE INVENTION

In health care, there has been an increased emphasis on more widespread use of diagnostic tests involving biological fluids, especially in the area of infectious diseases. Administering treatment in the fashion referred to as "therapeutic trials" rather than one based on a clear etiology is becoming more disfavored all over the world. There are several key disease related targets of interest including: nucleic acids, proteins, and metabolic signatures either individually or in combination with each other. Of particular importance are the antibody based tests, since they are well established as very specific and powerful for a wide range of disease detection. Since the basic need of a diagnostic test in general is for a rapid, inexpensive, convenient, and accurate decision making method that can advise whether to begin therapy, one step antibody tests have been developed for several decades and continue to have expanded applications in many different formats.

The current antibody based, in vitro diagnostic technologies (IVDT) vary from the elegantly simple lateral flow immunoassays to instrument intensive systems such as ELISA. While lateral flow assays are inexpensive and mobile and can serve many needs due to their reasonable sensitivity, they have many drawbacks. On the other end of the spectrum, manual microplate or robotic immunoassays with special fluorescent or chemiluminescent markers provide greater sensitivity, quantitation, documentation of results, and higher specificity. The emerging technology of microfluidic immunoassays are focused on retaining the benefits of microplate/robotic systems while providing portability, decreasing sample size, enhanced automation, and lowering costs. However, commercial systems have been slow to develop since microfluidics and associated technologies are in early stage development, in part since miniaturization poses new challenges in choice of materials, control and detection equipment, and operability.

What has not been investigated much or developed, are hybrid platforms that make use of natural driving forces while employing low power, simple instrumentation for improved sensitivity, quantization, and documentation. Interestingly, readers for lateral flow systems have recently become more popular in order to improve sensitivity and avoid misinterpretation by human readers. While companies are increasingly making them available for their specific lateral flow format, this approach does not represent a holistic approach to integrating natural driving forces with instrument based interpretation of the biological recognition event.

SUMMARY OF THE INVENTION

This invention is directed to the use of thermodynamically incompatible surfaces in agglutination assays for the express purpose of using the sample as a key component of the detection instrument. Specifically, the invention relates to formation of a lense and a virtual container for rapid mixing via thermal energy by a sample liquid disposed on superhydrophobic surfaces, and a subsequent immunoassay of a trace constituent using an antigen-antibody reaction for use in the industrial, environmental, and clinical laboratory test fields.

The invention operates by placing a drop of nano or microparticles on top of a drop of biological fluid on a superhydrophobic surface. The superhydrophobic surface is patterned using a hole, defect, post, or depression in order to rigidly hold the liquid sample in place. The sample forms a spherical drop that acts as a lens due to surface tension. A LED shines on the drop while nano or microparticles aggregate rapidly if the analyte is present, scattering the light and generating a detectable signal. The combination of drop geometry, convection currents, and increase of the intensity due to focusing, allows for a very wide range of detection from very low to very high particle and analyte concentrations simply by measuring the intensity of the forward light focused by the drop.

In one embodiment, the invention provides a method for determining the presence of an analyte in a liquid biological sample such as blood, plasma, serum, urine, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, prostatitc fluid, or a combination thereof, comprising the steps of: contacting the sample with a binding substance specific to the analyte sought to be determined, which is optionally immobilized on a colloidal nano or microparticle of known size and/or size distribution; depositing the sample on a surface that is thermodynamically incompatible with the bulk liquid of the biological sample (i.e. superoleophobic for an organic bulk sample or superhydrophobic for an aqueous bulk sample), thereby forming a bead having a contact angle with the surface of no less than 150°; exposing the liquid biological samples to an electromagnetic radiation source of known or tunable wavelength in parallel with the surface; and measuring the change in forward light scattering as a function of time using a detector positioned at the focal point collinear with the electromagnetic source, wherein a change in forward light intensity indicates the presence of the analyte.

In another embodiment, the invention provides a method of detecting an infectious disease in a subject, comprising the steps of: obtaining a liquid biological sample from the subject; contacting the liquid biological sample with a binding substance specific to the analyte which is pathognomonic of the infectious disease sought to be detected; depositing the liquid biological sample on a surface that is thermodynamically incompatible with the bulk liquid of the biological sample, wherein said liquid biological sample forms a bead having a contact angle with the thermodynamically incompatible surface; exposing the liquid biological sample to an electromagnetic radiation source; and measuring the change in forward light intensity as a function of time, wherein an increase in forward light intensity in the liquid sample, indicates the presence of the infectious disease.

In one embodiment, the invention provides a kit comprising: a biological liquid sample collection means; reagents, analyte specific binding substances immobilized on colloids of known particle size or size distribution, an electromagnetic radiation source; a detector; a superoleophobic surface;

a superhydrophobic surface; and instructions, the kit capable of performing the methods of the invention.

BRIEF DESCRIPTION OF THE DRAWINGS

The invention will be better understood from a reading of the following detailed description taken in conjunction with the drawings in which like reference designators are used to designate like elements, and in which:

FIG. 1 shows an aqueous drop on a superhydrophobic surface taking the shape of a sphere. When light passes through the drop, it focuses the light. Light is reflected in the drop if it is incident to the surface at an angle greater than the critical angle due to Snell's Law. Placing a detector at a focal point dictated by the angle of light leaving the drop generates a signal that varies depending upon the size of the particles in the drop.

DETAILED DESCRIPTION OF THE INVENTION

Figure 2A:
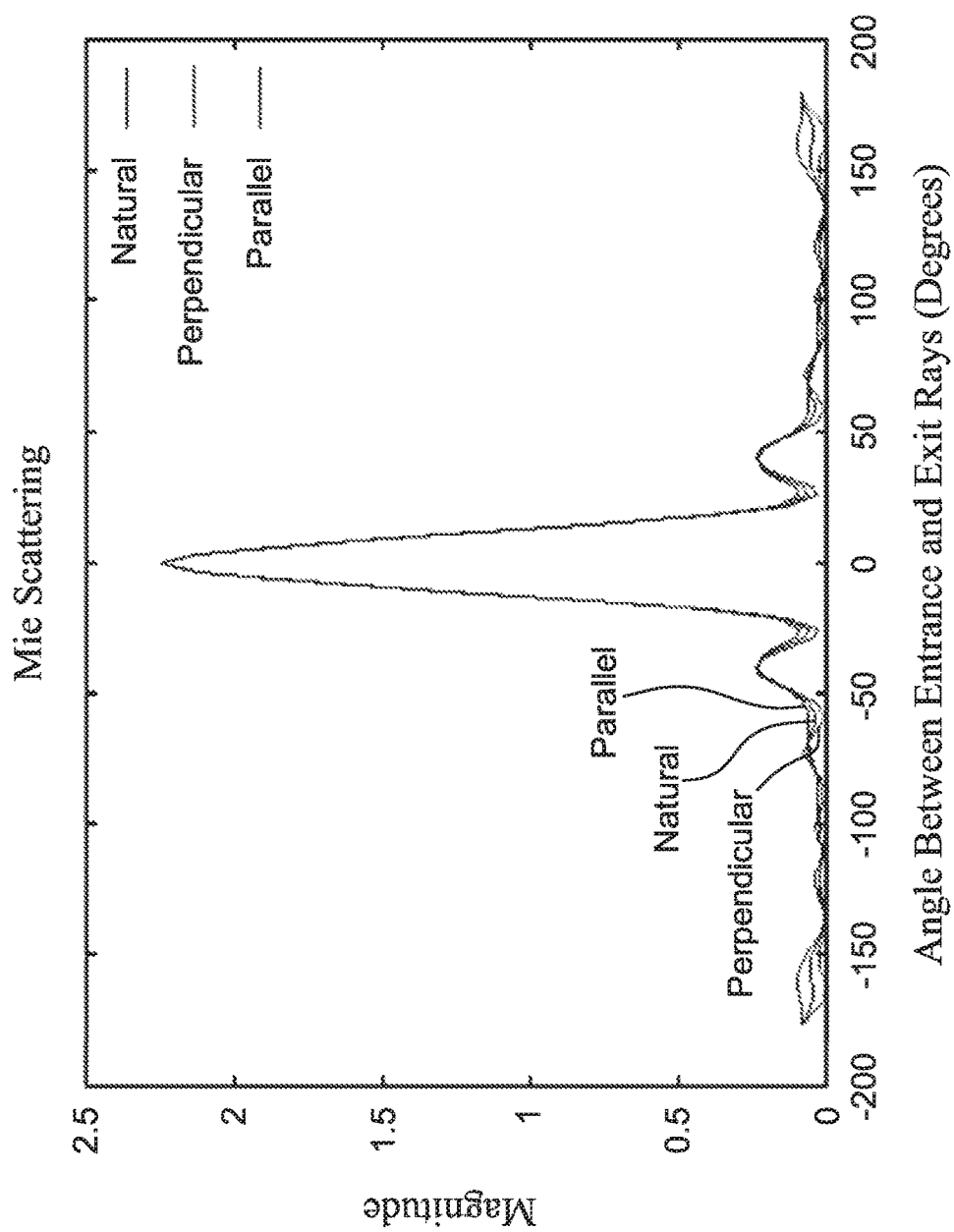
FIG. 2 shows linear graphs in which the unpolarized (natural), parallel, and perpendicular scattering of 500 nm light as a function of angle. Two different sized colloidal particles (a) 1 micrometer diameter and (b) 2 micrometer diameter.

In the present invention total protein or a specific antigen within a liquid sample is measured using an in vitro diagnostic device and method which relies on light scattering changes as nano or micro particles aggregate in the presence of total protein or a specific antigen which could be a protein, virus, bacteria, or polynucleic acid. These changes are detected through the focusing of light due to an aqueous drop, pinned and positioned on a superhydrophobic surface. A superhydrophobic surface is used to hold a patient's liquid sample, and integrates the patient's sample with the instrument by using that sample as a lens in order to focus a wide beam of light. The focusing of light increases the intensity of the light and can capture light from multiple reflections within the drop. Due to the amplification of the light intensity, the detection of total protein or a specific analyte is possible using very simple, low power electronics.

For the detection of a specific analyte, nano or microparticle direct or indirect agglutination is the basis for detection. In direct agglutination, particles agglutinate or aggregate due to the recognition of a specific ligand or antibody on the particle with a protein, virus, bacteria, polynucleic acid, or other analyte in the sample drop. For indirect agglutination, the presence of a peptide or other small analyte will disrupt the aggregation of nano or microparticles in the sample drop. In either method, aggregation will cause a change in the amount of light scattered and that change will be sensitively detected because the drop focuses the light for easy tracking of how the light changes over time. If no aggregation occurs, the light intensity focused by the drop will not change and that too is important information for calibration and as a negative or positive control for direct and indirect agglutination respectively.

For the case of total protein detection, the scientific basis for detection is the generation of nanoparticle aggregates induced by the presence of protein. This is due to a variety of interactions depending on the protein and the nano or microparticles, but it is particularly sensitive to molecules of the size, structure, charge distribution, and shape of proteins. While others have noted that light scattering can be used to detect the resultant aggregates of protein with nanoparticles (gold and iron, for example), the unique method for detecting these aggregates described here has, to the best of our knowledge, not been previously reported.

The following aspects of the detection of total protein using this invention are novel and noteworthy:
  placing a drop of nanoparticles on top of a drop of biological fluid on a superhydrophobic surface causes very rapid mixing generating a consistently changing signal influenced by protein concentration within a few seconds;
  a superhydrophobic surface that is patterned using a hole, defect, post, depression, or some combination of structures can rigidly hold in place a liquid sample while a low power light shining on one side of the drop is focused on the other side of the drop, boosting the intensity of the light and making it easy to measure the signal;
  the nanoparticles aggregate very rapidly, helped by the mixing due to convection currents at the surface of the drop where water evaporates driving small nanoparticles to the surface and leaving aggregates closer to the center of the drop
  due to the geometry of light traveling through the drop via refraction, there is a greater difference between the signal from a drop while aggregation occurs versus the signal possible from a cuvette sample holder given the same linear path length
  the combination of drop geometry, convection currents, and increase of intensity due to focusing, allows for a very wide range of detection from very low to very high particle concentrations (and hence protein concentration) simply by measuring the intensity of the forward light.

Superhydrophobic surfaces, both natural and artificial, cause aqueous drops to bead on them. The most water-repellent surfaces produce nearly perfect spheres with very little contact between water, solutes, and surface due to the roughness of the surface. Another phenomenon exploited in the present invention is that when nano or microparticles are present in the aqueous drop these particles remain highly mobile, and smaller-sized particles migrate to the drop surface due to both the driving force of evaporation and the expanded liquid/air interface. A newly identified, third useful optical property resulting from the suspension of an aqueous drop by the superhydrophobic surface is that a spheroidal lens is created. Without any additional energy or instrumentation, the simple placement of an aqueous sample on a superhydrophobic surface followed by the placement of a patient's liquid sample results in very rapid mixing and a means to detect and monitor analytes via agglutination.

Figure 3:
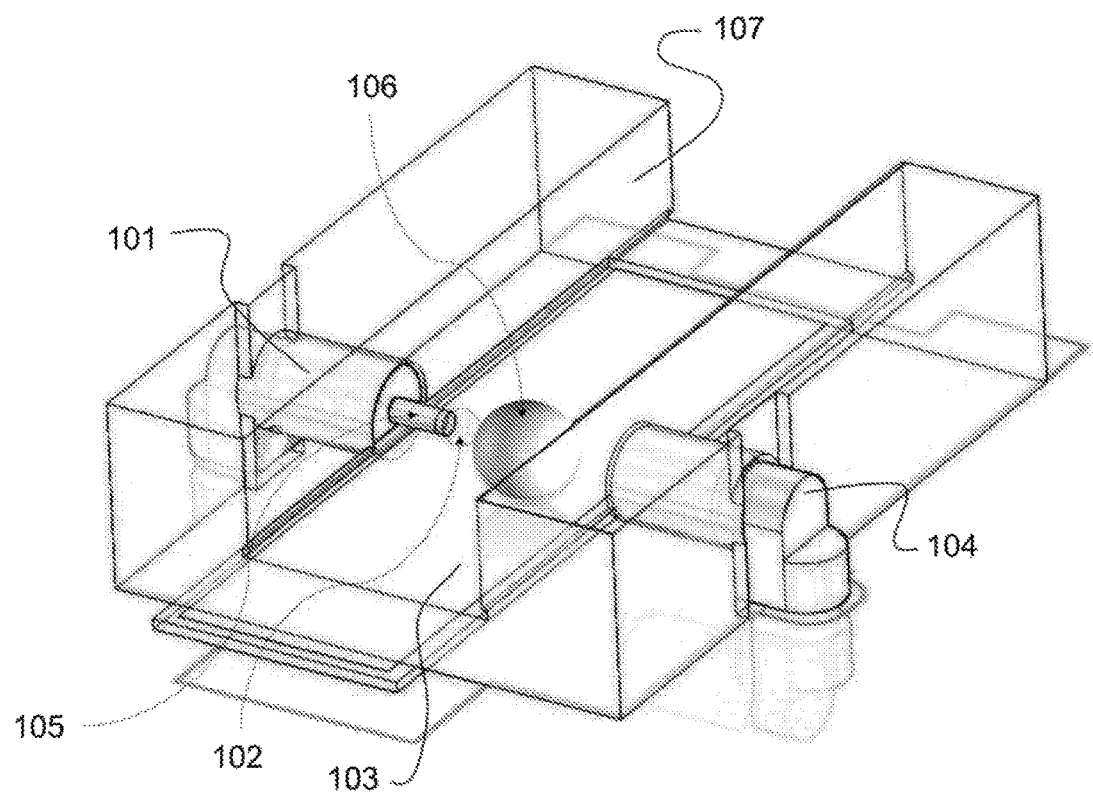
FIG. 3 shows an image of a working laboratory prototype with a near-IR LED 104 attached to a power source providing 1.9 V and 40 milliAmps; a matched, reversed LED detector 101 connected to an operational amplifier in order to boost the signal being measured by an ordinary voltmeter; and a drop of water 106; and a single block acrylic sample holder 107 fashioned to easily align the LED source and the detector; an ordinary borosilicate ball 102 attached to an optical fiber 105, which is used to collect and measure the light focused from the water drop making it easier to collect as much light as possible without special consideration to exact alignment of the fiber.

The images in FIG. 3 provide an illustration of a working laboratory prototype. The sample (in this case, for illustrative purposes, a water drop and a biological fluid drop with nanoparticles are shown) sits on a superhydrophobic surface that is patterned. A hole, defect, post, depression, or some combination of superhydrophobic or flat structures in order to rigidly hold in place a liquid sample can be used. A low power, near-infra red light emitting dioded (LED) can illuminate the drop and an optical fiber with a ball lens attached is used to collect the light and send it to a matched, reversed LED. An operational amplifier boosts the signal so that a low cost voltmeter can be used to measure the signal. The retail cost of all of the electrical components of the laboratory prototype is about $15-$20 dollars including batteries, making it an extremely low cost instrument compared to any point of care diagnostic device or light scattering detector. As can be visualized in FIG. 3b, the drop acts like a ball lens and the scattering and internal reflection properties of the drop along with the reflection and scattering of light incident to the superhydrophobic surface generates a signal. Even though a very high nanoparticle concentration is used in FIG. 3c, enough light is focused by the sample when proteins are present due to attenuated forward scattering as well as the movement of large aggregates towards the bottom of the drop (e.g., for extremely high analyte concentration drops).

The pilot data that is described in further detail in Example 2 shows that the methods of the present invention can be useful in detecting serum proteins levels that are elevated due a variety of conditions. With appropriate calibration of particle concentration and with a variety of clinical samples, it could also serve to screen for high protein levels in saliva. The nature of the nonspecific aggregation would make this simple reading difficult to use for exact quantitation, but it should suffice for providing important clinical decision making based on threshold values.

This invention relates in one embodiment to the use of superhydrophobic surfaces in agglutination assays. In another embodiment, the invention relates to formation of a lense and a virtual container for rapid mixing via thermal energy by a sample liquid disposed on a superhydrophobic surfaces, and a subsequent immunoassay of a trace constituent in the created lense, using an antigen-antibody reaction for use in the industrial, environmental, and clinical laboratory test fields.

In one embodiment, superhydrophobic surfaces, both natural and artificial, cause aqueous drops to bead on them with the most extremely water repellent surfaces producing nearly perfect spheres with very little contact between water, solutes, and the surface. In another embodiment, nano or microparticles in the aqueous drop are quite mobile and smaller sized particles migrate to the surface, due to the driving force of evaporation in one embodiment, the relatively high liquid/air interface area, and the interfacial characteristics of the particles themselves. In one embodiment the surface forces operating at the interface of an aqueous drop makes a sphere, the most thermodynamically effective shape, minimizing the volume-to-surface area ratio, thereby creating a spherical lens. Thus, in one embodiment, without any additional power or special instrumentation, placement of an aqueous sample on a superhydrophobic surface provides a unique environment which is otherwise difficult to reproduce by other means leading in one embodiment, to a new way to detect an agglutination process which is closely related to the lateral flow immunoassay format.

Analysis of agglutination immunoassays by instruments, rely on forward light scattering measurements since detection in immunoassay agglutination is based on antibody bound nano or microparticles recognizing an antigen in the sample and aggregating. As particles containing immobilized antibody encounter a suitable antigen, more than one particle binds forming aggregates that increase the amount of forward light scattered. Thus, in one embodiment, the instrumentation is either designed to measure scattered light or the amount of light transmitted over a specific cross-section of the liquid sample in another embodiment.

The images in FIG. 3 provide an illustration of a working laboratory prototype. The sample 106 (in this case, for illustrative purposes, a water drop and a biological fluid drop with nanoparticles are shown) sits on a superhydrophobic surface 103 that is patterned. A hole, defect, post, depression, or some combination of superhydrophobic or flat structures in order to rigidly hold in place a liquid sample can be used. A low power, near-infra red light emitting diode 104 (LED) can illuminate the drop and an optical fiber 105 with a ball lens 102 attached is used to collect the light and send it to a matched, reversed LED detector 101. An operational amplifier boosts the signal so that a low cost voltmeter can be used to measure the signal. The retail cost of all of the electrical components of the laboratory prototype is about $15-$20 dollars including batteries, making it an extremely low cost instrument compared to any point of care diagnostic device or light scattering detector. The drop acts like a ball lens and the scattering and internal reflection properties of the drop along with the reflection and scattering of light incident to the superhydrophobic surface generates a signal. Even when a very high nanoparticle concentration is used, enough light is focused by the sample when proteins are present due to attenuated forward scattering as well as the movement of large aggregates towards the bottom of the drop (e.g., for extremely high analyte concentration drops). A single block acrylic sample holder may be fashioned to easily align the LED source and the detector. A drop of biological fluid may be analyzed using 200 nm amino polystyrene divinylbenzene particles with amino groups. When the light is turned on, some red light may be visible since the LED has a fraction of its total light emission in the visible range.

Figure 2B:
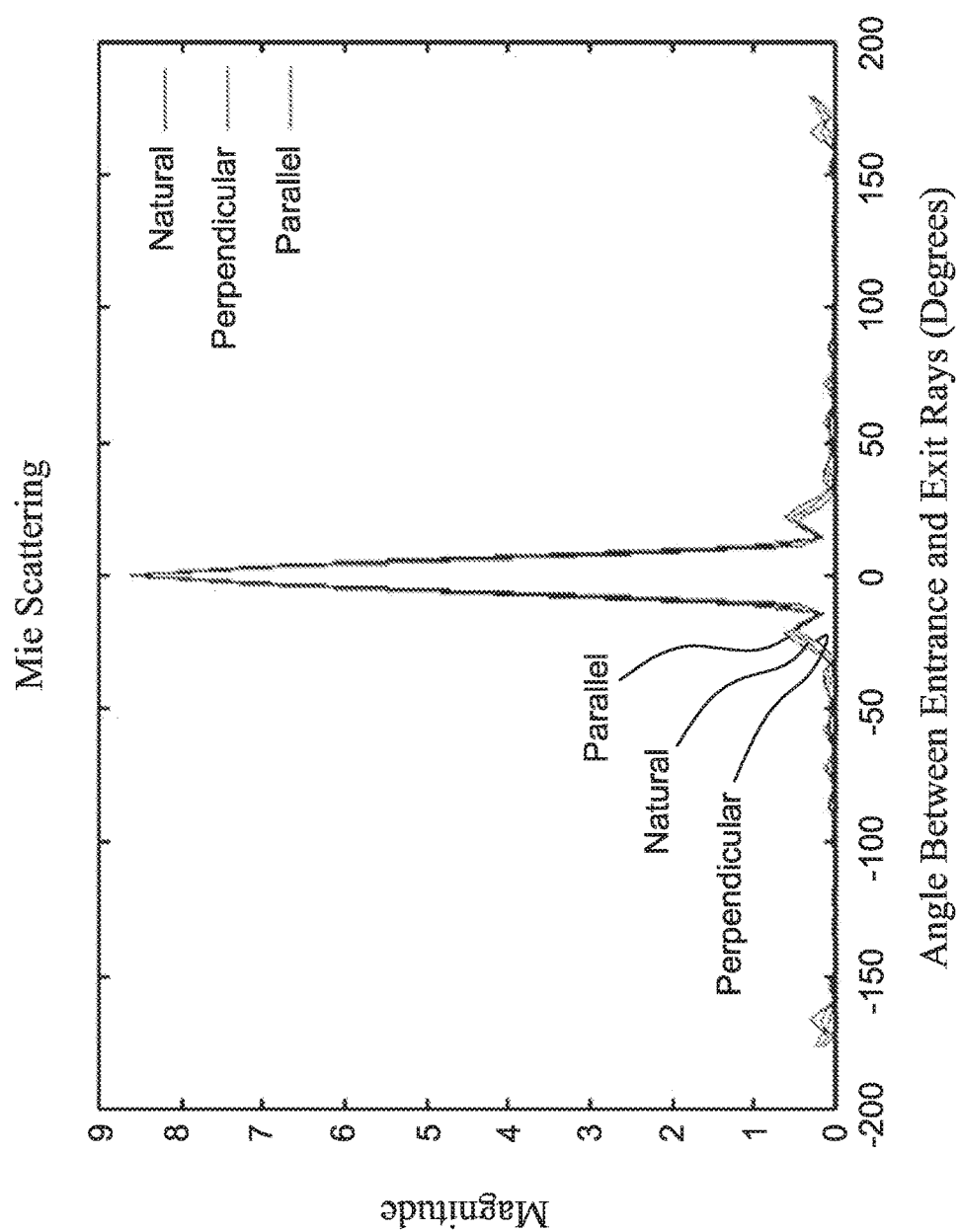

When nano or microparticles of a size comparable to the wavelength of light are used in the agglutination assay, particles with a diameter much smaller than the wavelength of light scatter light relatively equally in all directions while those comparable to the wavelength of light undergo an attenuated scatter pattern favoring the forward direction. For a 1 µm colloidal particle, most of the scattering intensity is directed at ±25° from the horizontal axis for 500 nm light (see FIG. 2). For colloidal particles of 100 nm or less, the intensity distribution for this wavelength of light is very broad. In one embodiment, assuming a visible light wavelength is used as the incident light source and colloidal particles of about 100 nm are used in the biological sample, a progressive decrease will be observed in backward light scatter as the colloidal particles agglomerate to create a particle network of a size equal to between about 700 and 750 nm.

In one embodiment, internal reflection rather than refraction occurs when the incident light from the aqueous solution to air interface exceeds a critical angle. According to Snell's law, for a ray of light traveling from water to air, an incidence angle greater than about 49 degrees results in internal reflection since the sine of an angle cannot exceed a value of 1. Light that is scattered from particles that have a broader scattering intensity band will have in one embodiment, a larger fraction of light reflected rather than refracted as compared to larger particles or agglomerates. Thus, the present invention has the advantage that the attenuation of scattered light accompanying agglutination of particles (e.g., larger particles are formed and smaller particles disappear) leads to less reflection of light and more light reaching the detector. Accordingly, the increase in light intensity reaching the detector disposed at the focal point collinear to the illumination source passing through the lens formed of the biological liquid sample, is indicative of agglutination and correlates to the presence of the protein or analyte being detected in biological sample and may be measured using the methods and kits described herein.

Accordingly, provided herein is a method for determining the presence of an analyte in a liquid biological sample, comprising the steps of: contacting the liquid biological sample with a binding substance specific to the analyte sought to be determined; depositing the liquid biological sample on a surface that is thermodynamically incompatible with the bulk liquid of the biological sample, wherein said liquid biological sample forms a bead having a contact angle with the thermodynamically incompatible surface of no less than about 150°; exposing the liquids biological samples to an electromagnetic radiation source; and measuring the change in forward light intensity as a function of time, wherein an increase in turbidity in one embodiment, or forward light scattering or both in the liquid sample, indicates the presence of the analyte.

Super-hydrophobic and super-oleophobic materials are characterized in one embodiment, by reference to a water contact angle with the surface of the material. A water contact angle which is greater than about 120 degrees is considered in one embodiment, to be indicative of a super hydrophobic material. In another embodiment, super hydrophobic materials exhibit a water contact angle in the range of about 150 degrees. A super-hydrophilic material is characterized in one embodiment, by a water contact angle of 0 (zero) degrees, which results in an instantaneous wetting of the surface of such a material. Accordingly and in one embodiment, an aqueous liquid biological sample forms a bead having a contact angle with the thermodynamically incompatible surface which is superhydrophobic (SH), of no less than about 150°. In another embodiment, an organic liquid biological sample forms a bead having a static water contact angle with the thermodynamically incompatible surface which is superoleophobic (SO), of more than about 120°.

Hydrocarbon polymers used as superhydrophobic surfaces include in certain embodiments polymers derived from one or more olefinic monomers, oligomers, or polymers. In another embodiment suitable hydrocarbon polymers are silicone polymers, polyolefins and their copolymers such as ethylene, propylene, diene terpolymer (EPDM) rubbers, and acrylate polymers. In one embodiment, representative olefinic monomers, oligomers, or polymers include carbon-containing compounds having at least one site of unsaturation. The olefinic monomers, oligomers, or polymers comprise or include in certain embodiments; a mixture of polyolefins, (meth)acrylate esters, allyl ethers, vinyl esters, vinyl ethers and the like. Epoxy resins may also be used as a binder. In one embodiment, the surface used in the methods and kits provided herein, is coated with silicone compounds; silanes, fluorocarbon polymers, perfluoroalkyl ethyl methacrylate (PPFEMA) coated polycaprolactone, hydrocarbons, polymer mats made of polystyrene and poly[tetrafluoroethylene-co-(vinylidene fluoride)-co-propylene] (PTVFP); polyethylene glycol with glucose and sucrose in conjunction with a hydrophobic substance; combinations of nanoparticles with polyethylene or polypropylene; high density polyethylene, technical waxes; films of rough particles of metal oxides, polymer binder layers containing a plurality of porous protrusions, or a combinations thereof.

In one embodiment, the binding substance, specific against the analyte sought to be detected or determined in the methods and kits provided herein, is immobilized on nano or microparticles of a known size or size distribution. In another embodiment, binding substance, specific against the analyte sought to be detected or determined in the methods and kits provided herein, is a monoclonal antibody.

The term "particles" refers in one embodiment, to microparticles, or nanoparticles or mixtures thereof in other discrete embodiments. In one embodiment, the term "microparticles" refers to particles having an average particle size of about 0.1 to about 100 μm. The term "nanoparticles" refers in another embodiment, to particles having an average particle size of about 1 to about 100 nm. In one embodiment, the size of the microparticles or nanoparticles is significantly smaller than the distance between the raised portions in a micropatterned surface. In one embodiment, particles suitable for practicing the invention are microparticles, nanoparticles or a mixture thereof having an average particle size of from about 5 nm to about 100 μm. In another embodiment, the particles can have an average particle size of from about 50 nm to about 700 nm, or in another embodiment, between about 200 and 800 nm, or in another embodiment, between about 400 and 750 nm, each a discrete example of the colloidal particles on which the binding substance is immobilized on. The term "average particle size" refers to the size of primary particles, as they would be classified by means known in the art, and is not the size of agglomerates.

In one embodiment, the electromagnetic radiation source used in the methods and kits provided herein has a narrow wavelength. In another embodiment, the narrow wavelength may be achieved using filters or LED light of a particular color. In one embodiment, the selection of the wavelength emission window will be a function of the size or size distribution of the nano or microparticles upon where the analyte-specific binding substance is immobilized. Accordingly, in one embodiment, the particle size is between 400 nm and 600 μm and the LED light used is yellow, emitting at 570-590 nm, or in another embodiment, the particle size is between about 600 nm and 750 nm, and the LED light used is red. In one embodiment, the size or size distribution of the colloidal particles used will necessitate the use of a wider wavelength window, which can be achieved in another embodiment with the selection of more than one LED color or the appropriate filters.

The specific analyte sought to be determined or detected in the methods and kits provided herein, is not particularly limited as long as the substance that specifically binds to the analyte can exist; and in another embodiment, can be immobilized onto the nano or microparticle. Embodiments of the analyte include proteins such as albumin, or hemoglobin, hemoglobin A1c, myoglobin, transferrin, lactoferrin, cystatin C, ferritin, .alpha.-fetoprotein, carcinoembryonic antigen, CA19-9, prostate-specific antigen, C-reactive protein (CRP), fibrin degradation product (FDP), pepsinogens I and II, and collagen; lipoproteins such as high-density lipoprotein, low-density lipoprotein, and very low-density lipoprotein; nucleic acids such as deoxyribonucleic acid and ribonucleic acid; enzymes such as alkaline phosphatase, lactate dehydrogenase, lipase, and amylase; immunoglobulins such as IgG, IgM, IgA, IgD, and IgE; antigens and antibodies associated with infectious diseases, such as hepatitis B virus, Dengue fever virus, hepatitis C virus, human immunodeficiency virus, and *Helicobacter pylori* and antibodies thereto; drugs such as haloperidol, risperidone and bromperidol; hormones such as sex hormones; cell surface polysaccharides specific to bacteria, yeast and other pathogens such as lipopolysaccharides; and polynucleotide sequences such as DNA and RNA strands that are specific to a bacteria or virus that can be used to identify a pathogen via its genetics, each a discrete and non-limiting embodiment of the specific analyte sought to be detected or whose presence is sought to be determined by the methods and kits described herein.

In the binding reaction between the analyte and the specific binding substance and the agglutination reaction of the bound matter, reaction conditions such as the reaction temperature, the pH, the type of liquid biological sample, the type of coexistent salt and the concentration thereof, and other coexistent substances are the same as those in conventional immunological and/or agglutination assays.

In one embodiment, "electromagnetic radiation" refers to waves of electric and magnetic fields. Electromagnetic radiation used in certain embodiments of the methods and kits provided herein, are in certain embodiments, light, infrared light, UV light and the like.

In one embodiment, the biological sample in which the analyte is determined in the kits and methods provided herein, is blood. In another embodiment, the biological sample is plasma, or serum, gastrointestinal secretions, homogenates of tissues or tumors, synovial fluid, feces, urine, saliva, sputum, cyst fluid, amniotic fluid, cerebrospinal fluid, peritoneal fluid, lung lavage fluid, semen, lymphatic fluid, tears, prostatitc fluid, or a combination thereof in other discrete embodiments of the liquid, or in another embodiment, semi-liquid biological samples wherein an analyte is determined using the kits and methods described herein. In one embodiment, the biological samples transmit light through, in an amount sufficient to be detected by a detector. In another embodiment, the methods described herein, further comprise positioning a detector at a focal point colinear to the electromagnetic radiation source.

In one embodiment, the selection of a thermodynamically incompatible surface will be determined based on the biological sample taken from the subject or a pool of subjects. In one embodiment, blood is a hydrophilic substance and will form a sphere-like lens on a superhydrophobic surface. In another embodiment, an organic solvent to extract membrane proteins will form a spherical lens after beading on a superoleophobic (SO) surface provided in the methods and kits described herein.

In one embodiment, the step of measuring the change in focused light intensity as a function of time in the methods described herein, is preceded by a step of depositing another portion of the same liquid biological sample on the thermodynamically incompatible surface with the same nano or microparticle concentration, however in the absence of the binding substance. In one embodiment, the step of measuring the change in focused light intensity as a function of time comprises comparing the changes in forward light scattering between the samples. In one embodiment, migration of nano or microparticles to the surface of the liquid biological sample will change the curvature of the lens created and will require refocusing the detector in one embodiment, or reducing the light scattering of the "blank" sample. A person skilled in the art would readily recognize that depending on the interfacial properties of the biological sample analyzed, the nano or microparticles may migrate in certain embodiments to the interface between the biological sample and the thermodynamically incompatible surface, thereby modulating the contact angle between the sample and the surface, affecting the scatter pattern of the incidental light transmitted through the sample. In those cases and in one embodiment, depositing a blank sample where no analyte-specific binding substance is present, serves as a reference.

In one embodiment, the temperature differential between the sample and the surface creates convective currents whereby, in the presence of the colloidal particle, a thorough and uniform mixing of the particles occurs. In one embodiment, convection currents occur in the liquid biological samples described herein since some region of the liquid has a temperature gradient in it, such as the one resulting from evaporation at the sample interface in certain embodiments. This causes some part of the liquid to have a different density and, due to hydrostatic pressure differentials; the liquid begins to accelerate if it's hotter. In one embodiment, the addition of the colloidal particles having the analyte specific substance immobilized theron, to the biological sample that has formed the lens, induces rapid convective mixing, ensuring in another embodiment, uniform mixing of the colloidal particles within the liquid sample. In one embodiment, the thermodynamically incompatible surface is heated, or cooled to a temperature different than that of the biological sample, to induce, accelerate and increase convective mixing within the sample.

In one embodiment, the methods and kits described herein are used to detect infectious diseases. In another embodiment, provided herein is a method of detecting an infectious disease in a subject, comprising the steps of: obtaining a liquid biological sample from the subject; contacting the liquid biological sample with a binding substance specific to the analyte which is pathogenomonic of the infectious disease sought to be detected; depositing the liquid biological sample on a surface that is thermodynamically incompatible with the bulk liquid of the biological sample, wherein said liquid biological sample forms a bead having a contact angle with the thermodynamically incompatible surface of no less than about 150°; exposing the liquid biological samples to an electromagnetic radiation source; and measuring the change in focused light intensity as a function of time, wherein an increase in turbidity in one embodiment, or forward light scattering in another embodiment, or both in the liquid sample, indicates the presence of an infectious disease.

In one embodiment, the methods provided herein are capable of being performed by the kits provided herein. In another embodiment, provided herein is a kit comprising: a biological liquid sample collection means; reagents, analyte specific binding substances immobilized on colloids of known particle size distribution, an electromagnetic light source; a detector; a superoleophobic surface or a superhydrophobic surface or both; and instructions.

The following examples are presented in order to more fully illustrate the preferred embodiments of the invention. They should in no way be construed, however, as limiting the broad scope of the invention.

EXAMPLES

Example 1: Analysis

Experiments using 1 μm microparticles with immobilized antibodies to detect BSA in solution were completed; and a rapid increase in light intensity to the detector using a LDPE superhydrophobic surface have been tracked, while no such signal occurs using a flat LDPE surface. A change in intensity within less than 5 minutes was sufficient to generate a positive signal that scales with BSA concentration.

Having described preferred embodiments of the invention with reference to the accompanying examples, it is to be understood that the invention is not limited to the precise embodiments, and that various changes and modifications may be effected therein by those skilled in the art without departing from the scope or spirit of the invention as defined in the appended claims.

Example 2: Total Protein Determination Using Superhydrophobic Surface

The present invention shows a device and methods for measuring total protein in a sample from a subject using an in vitro diagnostic device that relies on light intensity changes as nano or microparticles aggregate in the presence of protein. These changes are detected through the focusing of light due to an aqueous drop, pinned and positioned on a superhydrophobic surface. A superhydrophobic surface is used to hold a patient's liquid sample, and integrates it with the instrument by serving as a lens that focuses a wide beam of light. The focusing of light increases the intensity of the light and can capture light from multiple reflections within the drop. Due to the amplification of the light intensity, the detection of total protein is possible using very simple, low power electronics.

FIG. 3 shows a working prototype of the invention known as the Integrascope. In order to reduce the invention to an example of total protein determination, a suspension of 20 nm diameter silver nanoparticles (Ted Pella) with a concentration of $7\times10^{10}$ particles per milliliter or 200 nm diameter amino polystyrene divinylbenzene particles (Polysciences) with a concentration of 2.5 Wt % were used. The method has only two steps. First a drop (20, 35, or 55 microliters) of BSA solution, human urine, saliva, or human serum was placed on the superhydrophobic surface. Then, a silver or amino PSDVB nanoparticle suspension drop of the same volume was placed on top of the biological sample drop, and voltage readings were immediately recorded as a function of time. A consistent signal is observed starting within a few seconds of placing the second drop and lasting at least several minutes. Mixing of the two drops generally appears to occur within 5-10 seconds and a slow convection current due to evaporation is the only bulk motion that seems to be present after that induction period.

Figure 4:
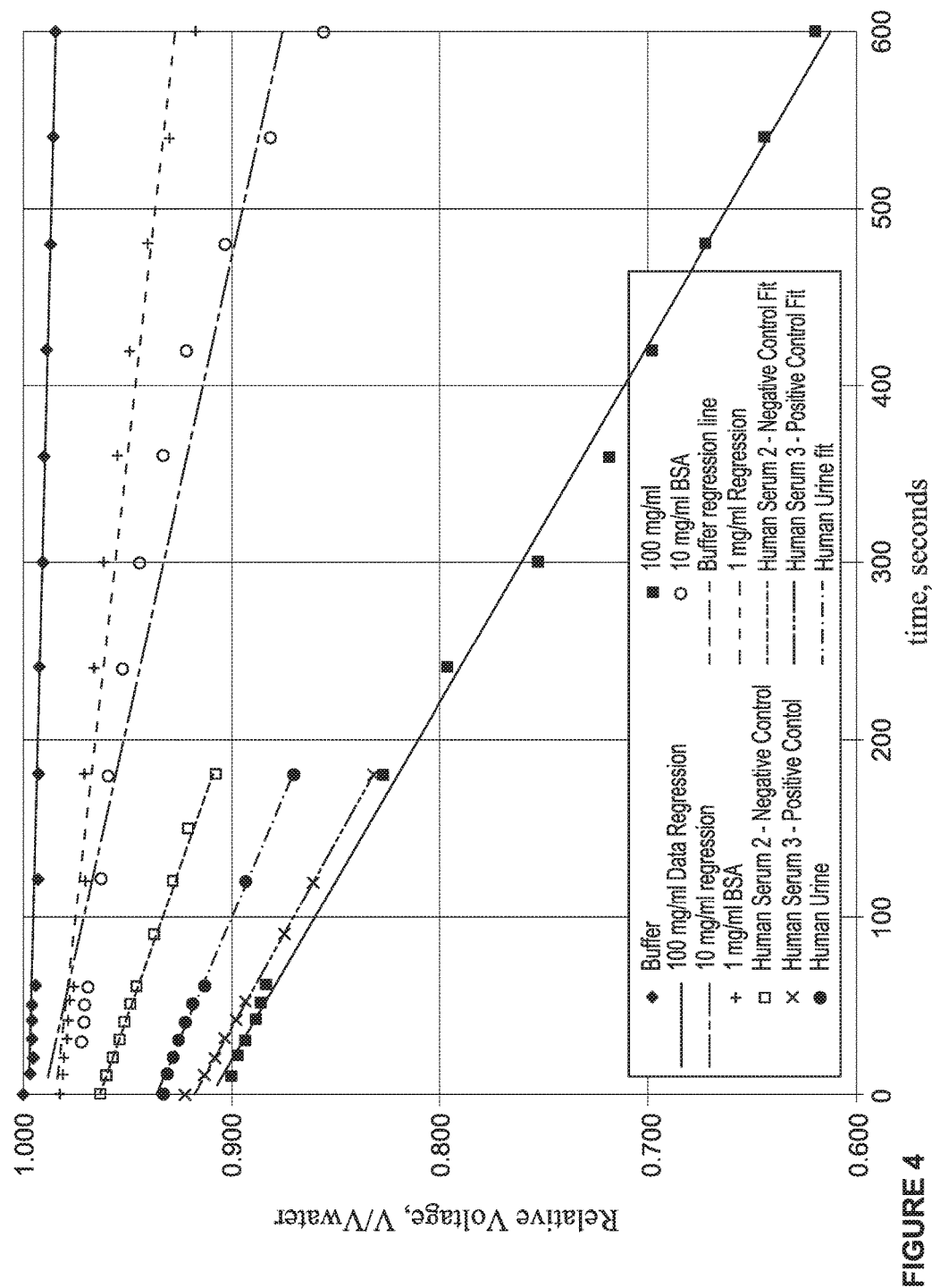
FIG. 4 shows an overview of protein detection using silver nanoparticles aggregating at a rate dictated by the total protein level in the sample with the aggregation tracked using light focused by the drop. The highest rate reflects the highest protein concentration used (100 mg/ml of BSA). The method is compatible with human serum and correctly identifys a human serum sample with an excess of protein due to high levels of C Reactive Protein as having a larger signal than a human serum sample without an excess of protein. A human urine sample also shows a high rate, possibly due to the creatinine content (about 1-3 mg/ml) as well as urea while a very small concentration of proteins less than 40,000 Daltons are usually present. Each type of sample will likely have different calibration curves due to the physical properties of the biological sample. However, these results clearly show the invention gives appropriate responses for samples containing protein.
Figure 5:
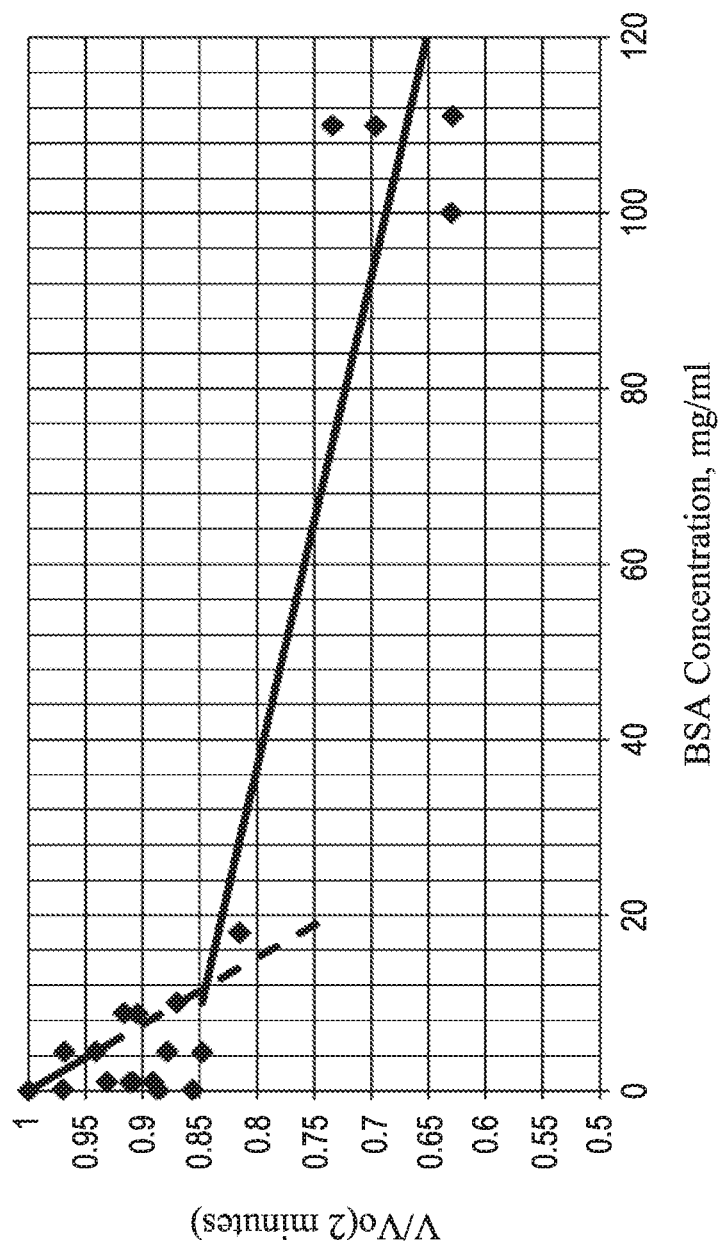
FIG. 5 shows a summary of data for samples with bovine serum albumin in a variety of buffer solutions being combined with a suspension of silver nanoparticles (20 nm). The data is given in terms of the voltage reading at 2 minutes after the drops are combined. The high degree of scatter and the general trend shown by the two lines are a result of the very low concentration of solver nanoparticles used. The method yields much better calibrations as the concentration of nanoparticles is increased (see FIG. 6).
Figure 6:
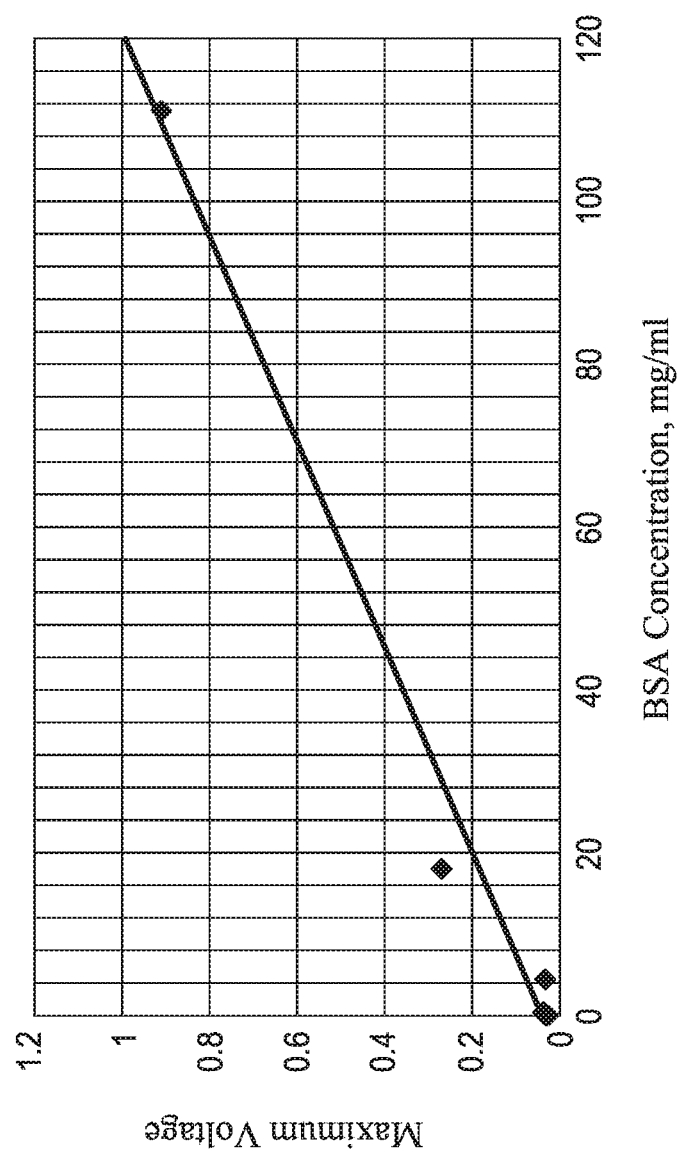
FIG. 6 shows a summary of data for samples with bovine serum albumin when combined with a suspension of amino PSDVB nanoparticles (220 nm). The data is given in terms of the maximum voltage reading which generally occurs between 10-20 seconds after the drops are combined. The reading reaches a maximum at that point since nanoparticles of this size range attenuate forward scattered light during the early stages of aggregation. Once the aggregates get bigger than several micrometers, the readings decrease due to the blocking of light. The high particle concentration ensures that there are more than enough particles available to give higher readings as the protein concentration increases.
Figure 7:
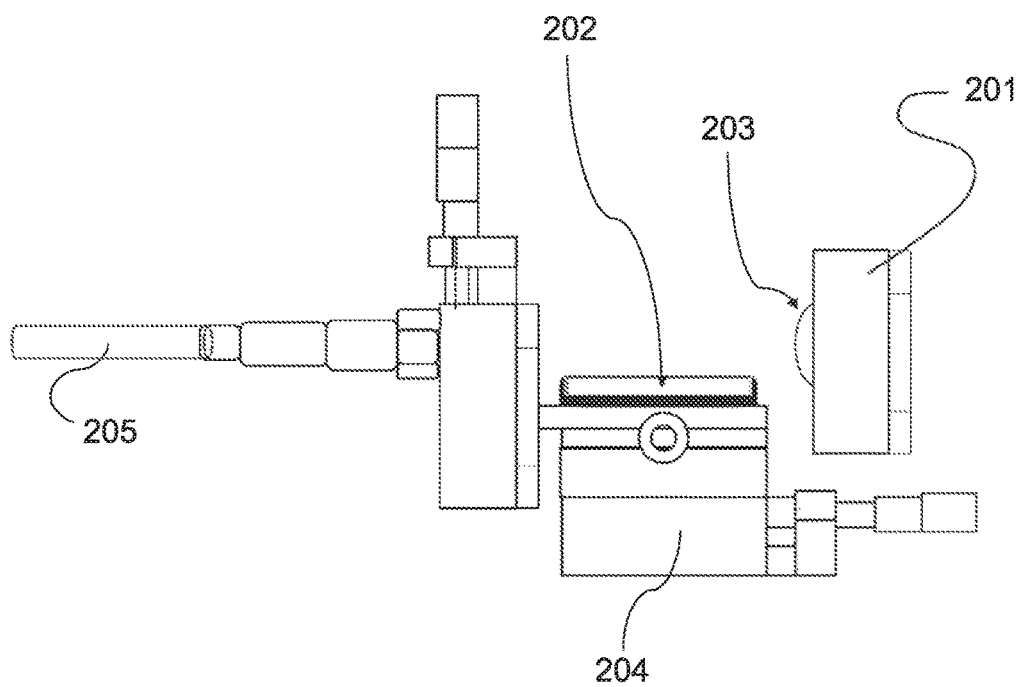
FIG. 7 Laboratory prototype—Integrascope. Two red/near IR light emitting diodes (LEDs) 203 and 205 are used to generate and detect light. A superhydrophobic surface 202 on support 204 between the two LEDs shapes a liquid sample into a sphere-like drop. The detector LED 205 receives the light from an 8 mm borosilicate glass ball attached to an optical fiber, as shown in FIG. 3. This makes the focused light from the sample simpler to acquire. The electronics include an operational amplifier and resistors in order to amplify the voltage signal detected by a voltmeter. The superhydrophobic surface 202 is patterned in order to hold the drop in a specific spot and not allow it to roll off the surface. The near infrared LED 203 is connected to a power source and is held in place by an acrylic block 201 near the superhydrophobic surface 202.

The data taken for different protein samples and two types of particles are summarized in FIGS. 4-6. It is clear from the data that adding a suspension of dilute 20 nm diameter, silver nanoparticles to water or a pH 7 buffered aqueous solution generates a slightly lower signal than simply using water, and it drifts lower with time at a very slow rate about the same as simply using two drops of water. This signal drift is very small and probably due to the very slow evaporation occurring in the system. However, it is also important to note that the superhydrophobic surface actually slows the overall rate of water drop drying compared to a regular surface due to the absence of a surface film and the presence of a stagnant layer of water vapor on the bottom half of the drop.

However, for the amino PSDVB 220 nm diameter particles the stock and ending concentrations (e.g., 2.5 Wt % and 0.54 Wt % respectively) are very high and the particles are larger thus scattering a great deal of light. The readings from a drop of amino PSDVB suspension and water or pH 7 buffer with no protein is very low and close to zero. With this system it is generally easier to see differences in the signal and there is very little change in the signal over time when no protein is present in the sample.

While it is clear that protein samples generate noticeably lower voltage signals than liquid without protein when silver nanoparticle are introduced (FIGS. 4-5). Most of the voltage decrease can occur very quickly—within the first 5-10 seconds—followed by a downward trend due to a secondary, slower dynamic process of silver nanoparticle aggregation. Since silver nanoparticles at the concentration and size used scatter very little light, aggregation leads to scattering of light and a lower voltage reading at the detector. FIGS. 4 and 5 are an overall compendium of data taken on a variety of samples. In these figures, the BSA solutions show much lower values with increasing protein concentrations. At very high protein concentrations, the silver particle concentration will need to be adjusted in order to have a more linear response because the silver nanoparticles will rapidly aggregate and with a limited number of particles further aggregation will not be possible thus generating a plateau in the voltage (see FIG. 6).

It is clearly shown in this example that human serum can be measured with this system. Mixing is very rapid even in these samples which have higher viscosity than simple protein buffered samples. Also, the signal is still present even though serum is not completely water-white. These findings indicate that serum with higher total protein due to the presence of abnormally high C Reactive Protein gives a much lower voltage signal. The protein levels of normal human serum are generally on the order of 30-70 mg/ml, while the positive control samples are at least 6 mg/ml higher due to the presence of an excess of C Reactive Proteins.

Human urine can also be used with this system. However it appears that this sample will have a different calibration as compared to serum and other biological solutions since constituents such as creatinine and urea will contribute in part to the signal generation. In any event, there is a reasonable concentration (several mg/ml) of protein of less than 40,000 Daltons in a typical sample as well.

However, given the high degree of scatter shown in FIG. 5 and the limited number of nanoparticles available for aggregation and hence protein detection, a sample of 2.5 Wt % amino PSDVB 220 nm diameter particles was used at a ratio of 15 microliters to 55 microliters of sample. In FIG. 6, a more reliable calibration is obtained simply due to the fact that attenuated forward scattering is only present when there are components that aggregate the particles. Buffer salts and water simply give a very low signal that does not drift over the two minutes that data is taken.

Given this more useful particle concentration for detecting proteins, several human biological fluid samples and a solution of urea matched to a typical urine concentration were measured and the data are summarized in Table 1. Overall, it appears that the serum protein levels measured seemed to be reasonably consistent and relatively accurate for the range of total proteins. However, the total protein in saliva should have been a little less than 1 mg/ml and the urine total protein is a little higher than normal—but that seems to be due to the presence of urea and possibly other components.

A more extensive set of experiments with gold, silver, and different latex nanoparticles can be performed to find optimize the right particle size and concentration to improve the calibration and better determine the level of confidence for total protein measurement in a wide variety of clinical samples. Experiments with clinical samples can be done in conjunction with clinical and analytical laboratory protocols in order to directly compare determinations with this simple, low cost method with more complex methods requiring expert systems and instrumentation.

TABLE 1

Readings and Predicted Total Concentration using 220 nm amino PSDVB particles

| | Saliva | NCOK | PCOK | PCNK | NCNK | Urea | Urine |
|---|---|---|---|---|---|---|---|
| Trial 1 | 0.11 | 0.361 | 0.437 | 0.413 | 0.163 | 0.08 | 0.047 |
| Trial 2 | 0.06 | 0.362 | | 0.424 | 0.127 | 0.031 | 0.098 |
| Trial 3 | | | | | | | 0.03 |
| Trial 4 | | | | | | | 0.089 |
| Averages | 0.08 | 0.36 | 0.44 | 0.42 | 0.15 | 0.06 | 0.07 |
| Predicted, mg/ml | 5.5 | 40 | 50 | 48 | 13 | 2 | 3 |

*NCOK and NCNK are negative controls for human serum from two different C Reactive Protein kits while PCOK and PCNK are the positive controls for each kit respectively.

Figure 11A:
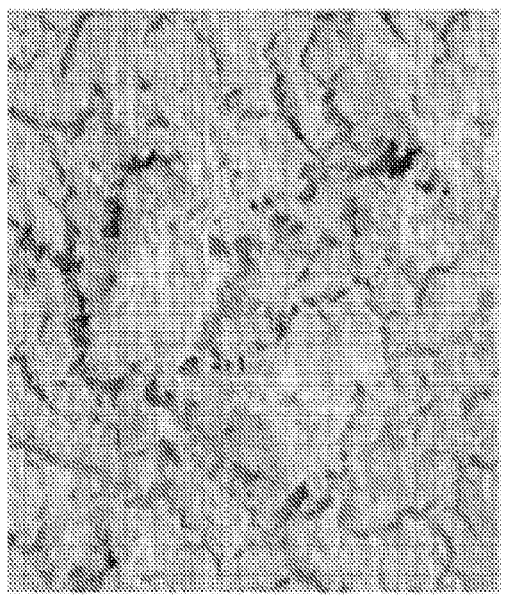
FIG. 11 A comparison of optical properties for drops on superhydrophobic (SHS) versus hydrophobic surface. Panel (A) is a 50.times. scanning electron microscope image of low density polyethylene (LDPE) converted into a superhydrophobic surface via solvent casting. Panel (B) shows the change in contact angle (CA) of water between the original LDPE surface and a superhydrophobic LDPE surface made by solvent casting. Panel (C) image (i) shows a close-up of the caustic generated by illumination of a 6 mm borosilicate glass sphere; image (ii) compares the caustic from the borosilicate glass sphere (top) with the caustic created by a water drop on a SHS LDPE surface (middle) and by a LDPE surface (bottom). Panel (D) shows that the light detected that is focused by the drop is stable for 2 minutes and does not change more than 1-2% for superhydrophobic after 10 minutes.
Figure 11B:
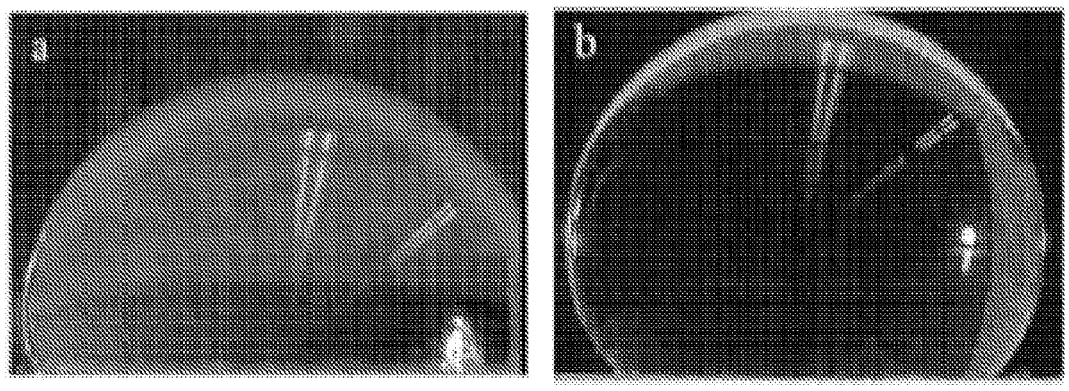
Figure 11D:
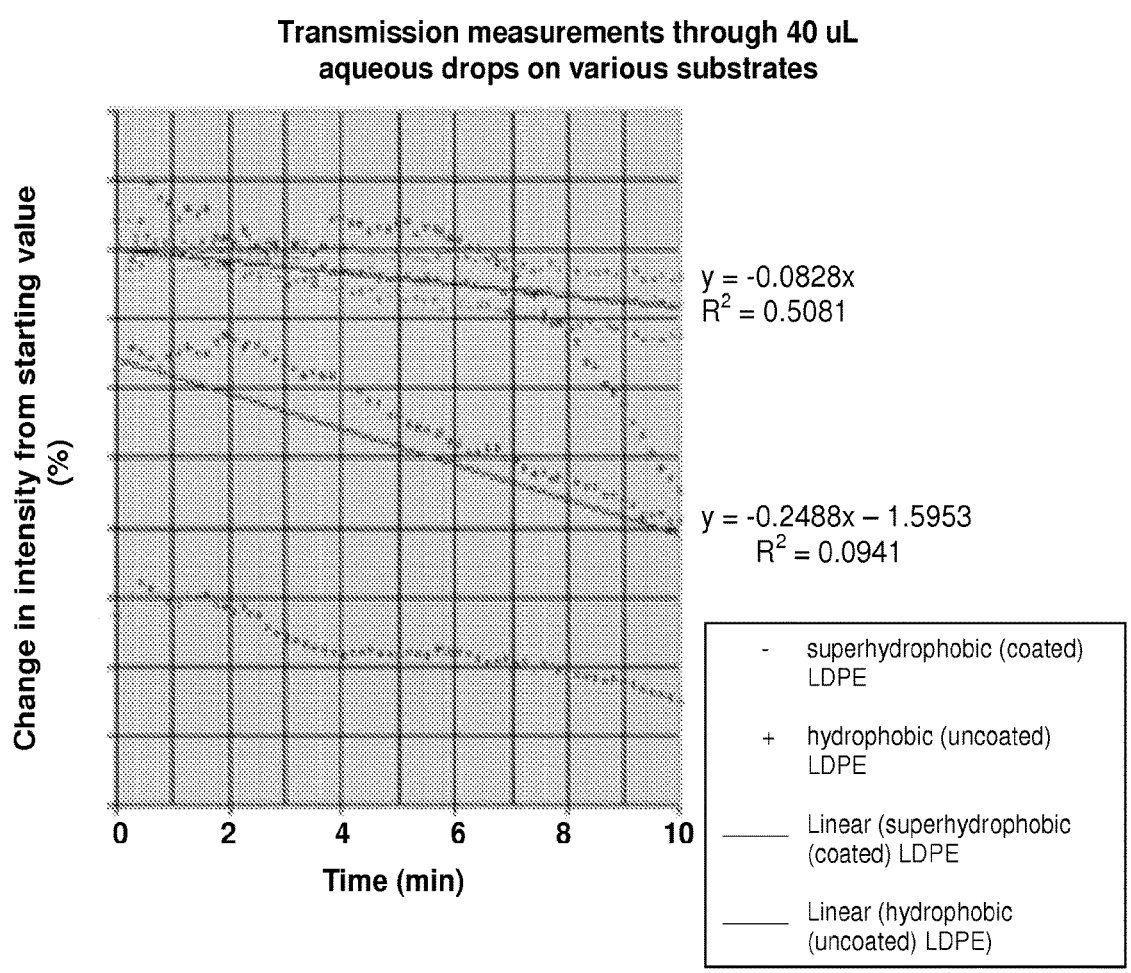
Figure 12A:
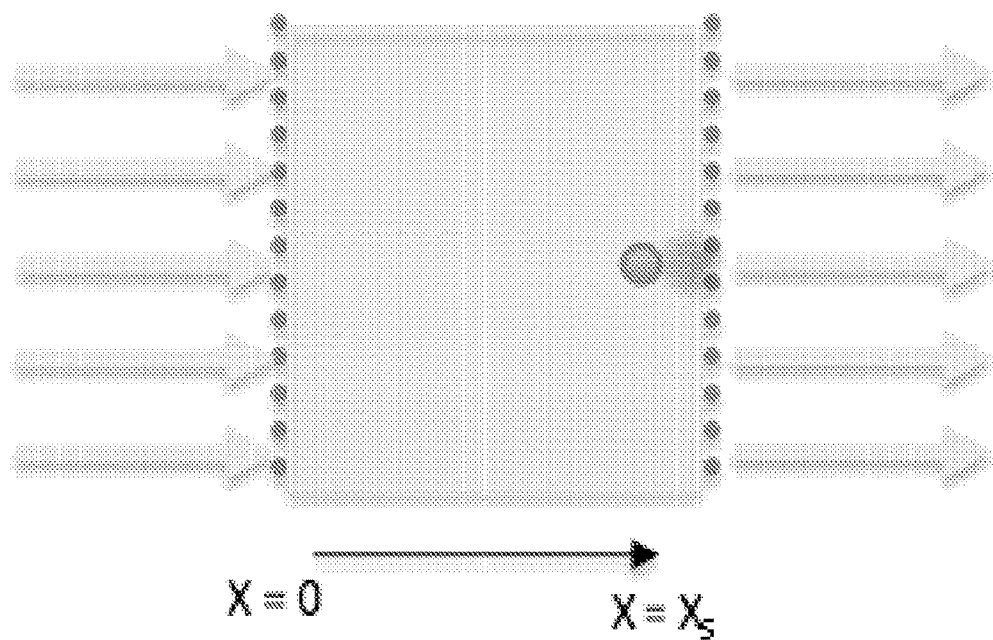
FIG. 12 Panels (A)-(C) are given to support the simplified model that illustrates why the drop is more sensitive to changes in light scattering as compared to a cuvette. Panel (A) is an idealized 2-D sketch of parallel light rays through a cuvette while Panel (B) is a simplified rendition of light being focused as a cone within a drop based on the ray tracing shown in Panel (C). In Panels (A) and (B) an object of circular projected area $A_S$ is considered to completely block the light incident upon it at $x_S$. The detector is assumed to be the same height and width for both cuvette and drop and the distance from the front edge of the drop and that of the edge to the detector is assumed to be the same for this analysis. In Panel (D) experimental evidence is given that light readings from a drop on a superhydrophobic surface are more sensitive to a change in particle size than a cuvette due to the focusing of light. The drop increases in signal by nearly 20% when 2 micrometer diameter particles are added to a suspension of 1 micrometer diameter particles at a ratio of 1:1,000 whereas the cuvette light signal increases by less than 1% which is a smaller increase than the experimental error due to small variations in the amount of liquid dispensed to create the mixture.
Figure 12B:
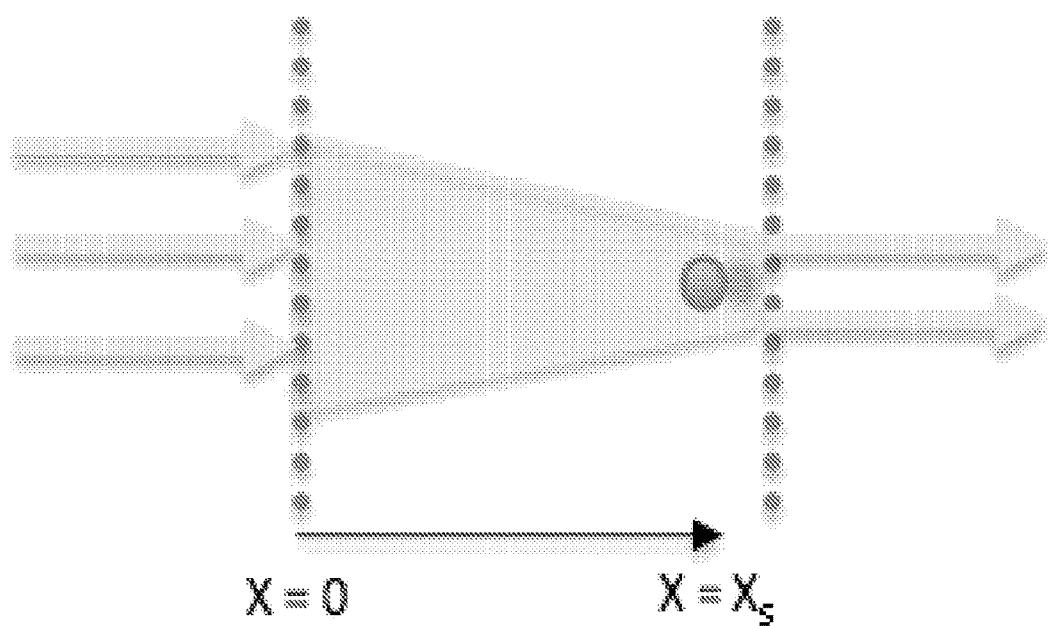
Figure 12C:
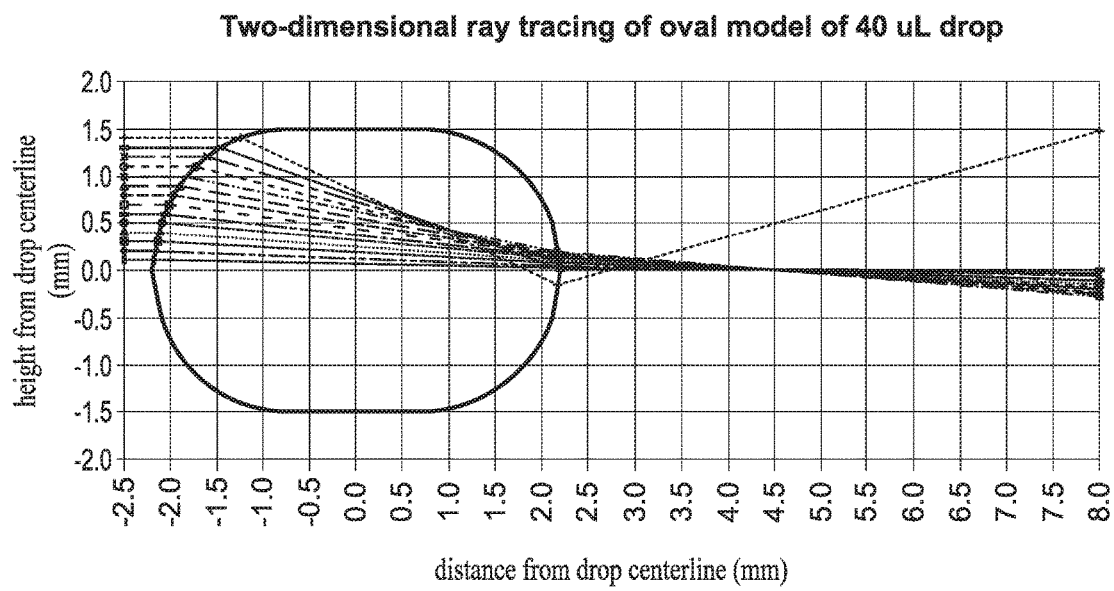
Figure 12D:
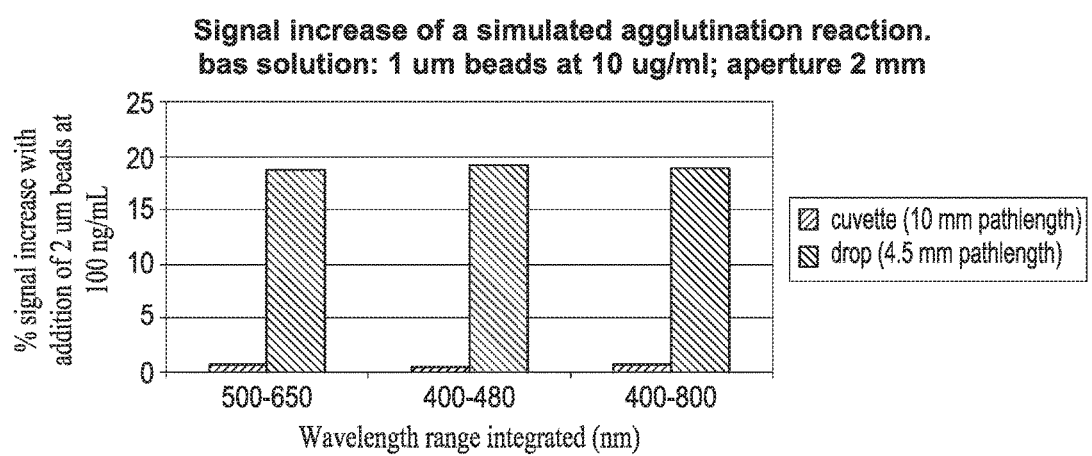

FIG. 11 show data using a second laboratory prototype device that employs a LED in the visible range (400-800 nm). In this second prototype, 100 uL drops delivered to fixed pinning site on superhydrophobic surface positioned between fixed light source and detector. Immediately following a protein drop trial, the surface was rinsed with the same volume of water. This served as a continuous "blank" correction as the drop contact angle, pinning site, and shape may have changed from drop to drop. These experiments did not employ particles and is used to show that light scattered from protein solutions can also be used in detection.

|  | | 1 mg/mL Myoglobin | | 0.5 mg/mL Myoglobin | | 0.25 mg/mL Myoglobin | |
| --- | --- | --- | --- | --- | --- | --- | --- |
|  | Water | Protein | Water Rinse | Protein | Water Rinse | Protein | Water Rinse |
| Trial 1 | 0.14 | 0.147 | 0.14 | 0.147 | 0.143 | 0.148 | 0.148 |
| Trial 2 | 0.142 | 0.149 | 0.14 | 0.148 | 0.144 | 0.147 | 0.147 |
| Trial 3 | 0.141 | 0.15 | 0.143 | 0.149 | 0.146 | 0.148 | 0.145 |
| Average | 0.141 | 0.149 | 0.141 | 0.148 | 0.144 | 0.148 | 0.147 |
| St. Dev | 0.001 | 0.002 | 0.002 | 0.001 | 0.002 | 0.001 | 0.002 |

*All Signal Reported in Volts

Example 3: Detection of C Reactive Protein in Serum

In the present Example, an exemplary device and method of the invention are described. A working Integrascope device that embodies the idea of using the patient sample is shown in the images below. The components are very inexpensive and the power usage is minimal. The LED uses red/near infrared light and is powered at 1.9 V and 40 milliamp current for the data presented in this example.

Figure 8:
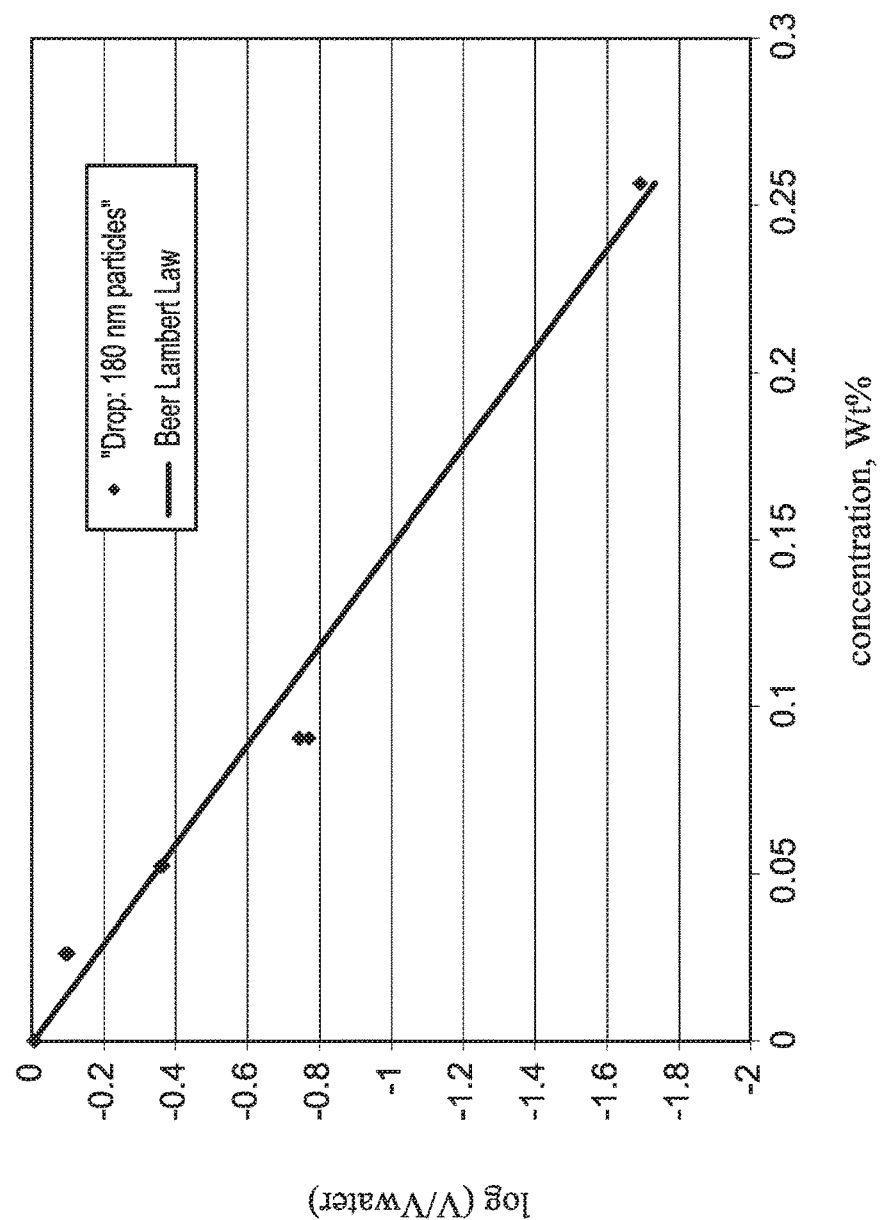
FIG. 8 Integrascope readings for 180 nm carboxylated polystyrene particles diluted with water from a stock solution of 2.65 Wt %. Each concentration was measured three times and a total of 8 measurements of pure water were taken between particle suspension readings to check consistency and reproducibility. A Beer Lambert law linear fit to the data is given for illustrative purposes. Based on the ambient lighting conditions, the detection limit for the y axis is a value of −2.4. The drop volume used was 40 microliters.

In order to establish the reproducibility, range, and sensitivity of the Integrascope shown in FIG. 3, a series of measurements with a known particle standard was collected. Carboxylated polystyrene particles of 180 nm average diameter (Polysciences) were diluted from a stock suspension of 2.65 Wt % and triplicate measurements were collected. FIG. 8 shows the data collected as the log of the ratio of the pure water reading versus readings at a specific particle concentration. The maximum reading for pure water was 1.19 V and the lowest reading at 0.024 V at a particle concentration of 0.26 Wt %. A one hundred fold change in the reading is shown in FIG. 8 with reproducibility in these experiments the range of readings at a specific concentration is within 2-3%. The system shows a very good sensitivity at low particle concentrations, but more importantly for agglutination detection, it also is sensitive to small changes in light scattering even when particle concentration is very high.

Many light scattering detector systems perform well at low particle concentration. However, due to the Integrascope's added dimension of focusing the light being passing through the drop and undergoing multiple scattering events at high particle concentrations, it can provide information on changes in particle scattering properties in very clear or very turbid suspensions.

A commercially available kit for the specific detection of C Reactive Protein (Fisher HealthCare Sure-Vue CRP Latex Test Kit) in human serum was used to establish the time dependent signal using the Integrascope with a well-established protocol for reading agglutination using a card and visual inspection. The kit contains a positive human serum sample of >6 mg/L of CRP and a negative human serum sample with <6 mg/L of CRP as a way to test the 100-150 nm diameter nanoparticles in the kit that contain immobilized anti-C Reactive protein antibodies as well as the technique of the operator.

Figure 9:
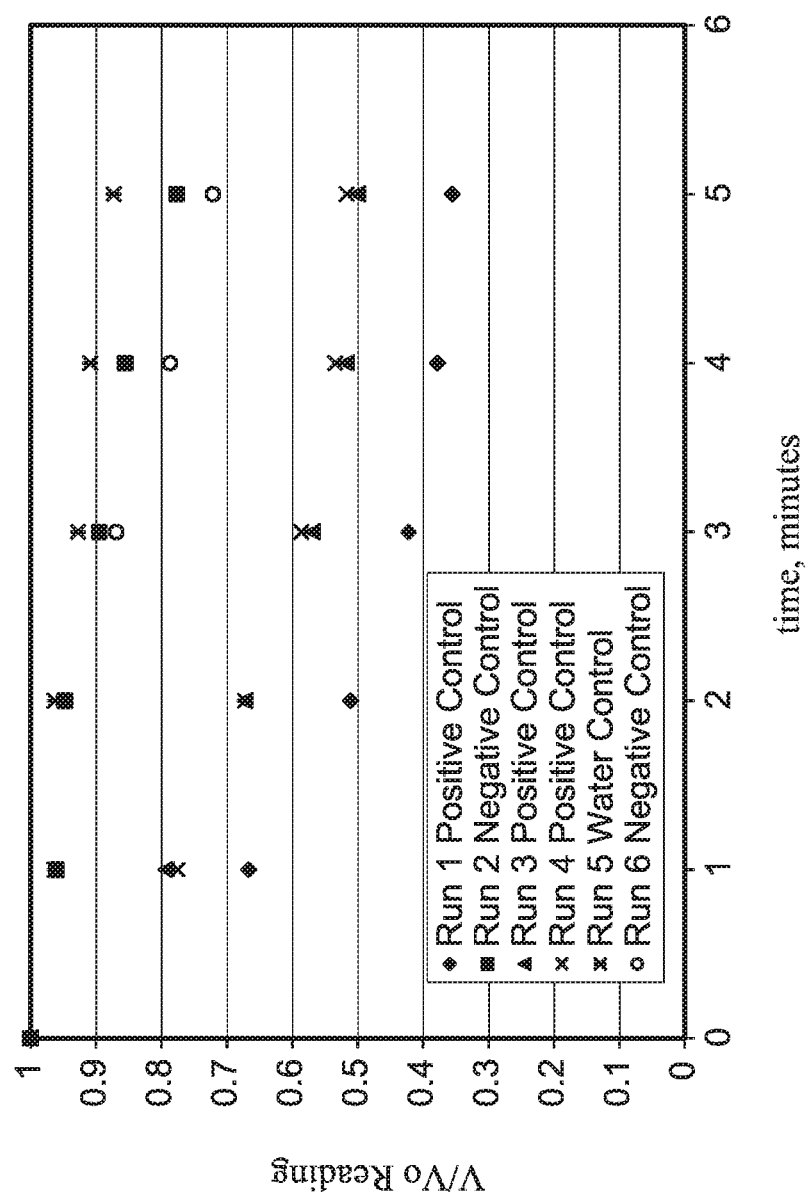
FIG. 9 Laboratory trials of the Integrascope with the Sure-Vue CRP latex Test Kit. The trials are listed in the order conducted. A 20 microliter sample of positive human serum, negative human serum, or water is first placed on the surface followed by a 20 microliter drop of anti-CRP latex nanoparticles placed on top of the first drop. Mixing is very rapid and the operator only needs to place two drops and wait for a reading. The same patterned, superhydrophobic surface is used with test drops removed by pipetting after 5 minutes and the surface is "washed" with a 40 microliter drop of pure water prior to the next trial. The readings after 5 minutes for the positive human scrum range between 0.3-0.5 V, while the reading after 5 minutes for the water and negative human serum samples are between 0.72-0.87 V.
Figure 10:
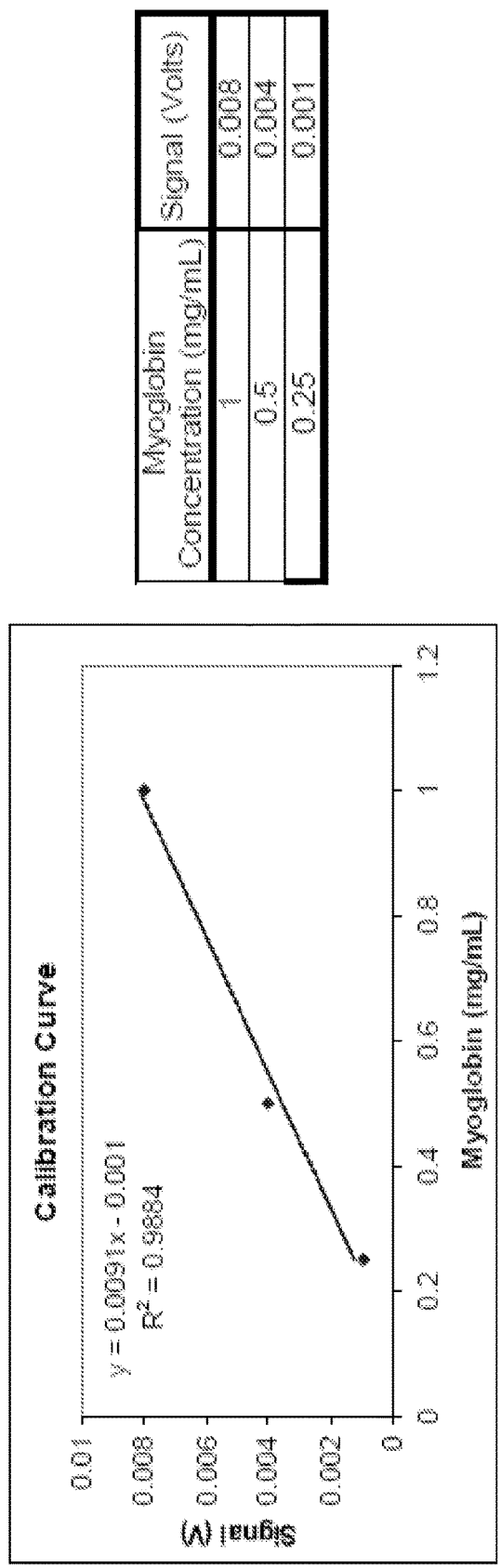
FIG. 10 Calibration of the system for detecting myoglobin protein concentration in water without the use of nanoparticles.

FIG. 9 shows the results of 6 separate trials with the contents of the Sure-Vue CRP latex Test Kit. In order to conduct the trials, first a 20 microliter drop of the biofluid sample (positive human serum, negative human serum, or distilled water) is placed on the patterned, superhydrophobic. Next, a 20 microliter drop of the 100-150 nm latex particle containing anti-CRP antibodies is placed on top of the sample drop. Due to the physics of superhydrophobic surface-water drop interactions, there a very rapid mixing event occurs so there is nothing else for the operator to do other than wait for the readings.

In FIG. 9, the data is given as a ratio of the reading within 2 seconds of placing the second drop and the reading at a specific time after the placement of the second drop. Clearly, the readings between water and negative serum vs. positive serum diverge within 1 minute. The data also show that the agglutination signal from the positive serum sample levels out by 5 minutes. The trials were conducted in the series given (Run 1-Run 6) with the removal of the test drop after five minutes followed by a "wash" of 40 microliters of water to test the readings. It is important to note that the negative human serum sample does contain a low level of C Reactive Protein (CRP) which likely will give a small agglutination signal. The water drop typical yields a very slow drift in reading after 5 minutes since the Integrascope laboratory prototype is not enclosed and no special provisions have been made to control evaporation or temperature changes.

The superhydrophobic surface appears to maintain its water-repellant and drop shaping properties throughout these readings. The sample drops are easily removed from the superhydrophobic surface by the use of a pipette and the surface shows no trace that aqueous drops were placed on its surface, understandably since there is very little interaction between the surface and the aqueous solutions.

This instrument can capture the very rapid change in signal as the nanoparticles are forming small clusters thereby attenuating forward light scattering before the clusters become large enough to block light. The average slope of the kinetic curves after 15 second for the positive control using visible light (e.g., fiber optic based detection system) is −0.15/min (+/−0.02) while the average slope for the positive control using near IR light (e.g., low-cost detector) was −0.19/min (+/−0.05). The negative controls show essentially no change in slope over this range and up to 5 minutes.

Example 4: Rapid Antigen Detection Using the Liquid Sample as a Lens and Self-Mixer for Light Scattering Detection The present Example provides further experimental evidence of the efficacy of the methods of the invention.

Of particular technological interest in point of care diagnostic methods for infectious disease detection in low resource settings has been the employment of particle immunoassays within lateral flow devices. These handheld, low cost devices are attractive because they are simple to use, powered solely by capillary action and can be read after a few minutes due to the collection of particles on control and readout lines, if the sample is positive for a particular antigen. However, the result of the test must be recorded by hand and high sensitivity can be difficult to achieve since at low antigen levels faint lines may be hard to read or because the immunoassay is designed for high specificity.

Particle-based immunoassays are also popularly employed in conjunction with detection instruments (i.e., nephelometers, light scattering detectors) and can determine the amount of light transmitted or scattered when an antigen is present through agglutination. These instruments can achieve a high degree of sensitivity based on the recording of time-resolved detection of light transmitted or by interpreting the light scattered at different angles. However, they can be too expensive as well as difficult to operate and maintain for clinics in developing nations. Encouraged by the ubiquity of low cost light emitting diodes and with new material science in controlling liquid interactions with surfaces, the inventors set out to design a simple low cost instrument that would use the patient sample and particle suspension in an integrative way in order to reduce cost and speed the detection of an antigen using nano or microparticle agglutination.

When a liquid drop is placed on a surface with microscopic and submicroscopic roughness, the liquid can be more attracted to itself than the surface causing a round drop to be formed on the surface. This phenomenon is referred to as superhydrophobicity or superoleophobicity depending upon whether the liquid is a water or oil, and a variety of surfaces with these properties are available. In the present invention, the particular interest was in superhydrophobic surfaces that generate spheroidal drops of biological fluids (e.g., whole blood, serum, urine, and saliva) and that can hold in place such drops while keeping interactions with the internal drop components at a minimum. Based on previous work [2, 4-6], low density polyethylene surfaces can be easily made into superhydrophobic surfaces through solvent casting. These superhydrophobic surfaces can organize particles suspended in the drop into opalescent spheres with smaller particles moving to the surface while larger particles reside mostly in the interior of the drop. The movement of particles within the drop and their organization suggested that this environment would prove useful to: (1) drive particle agglutination assays through a self-mixing process caused by slow evaporation; (2) segregate particles with different sizes; and (3) yield a unique optical environment as compared with standard cuvette or capillary flow systems.

The first step in developing the superhydrophobic drop agglutination immunoassay was determining the drop size and method to transmit and collect light at high sensitivity using relatively low cost optics and detection instrumentation. Work by Egri and colleagues [7] on how water drops on superhydrophobic surfaces focus sunlight confirmed our intuition that spheroidal drops would be useful (FIG. 11). Significantly, the formation of caustics in such a "lens" results in very high light intensity in the forward direction [8]. In comparison, a hydrophobic surface not only limits particle movement within the drop and generates more unwanted adsorption of components present in a drop, it also does not create a strong and easily detected signal when illuminated (FIG. 11).

Another consideration in the use of superhydrophobic drop agglutination detection is whether there is an inherent advantage over the use of a cuvette for the detection of changes in light scattered when agglutination occurs. When considering light passing through a cuvette or a straight capillary tube versus a spheroidal drop, the striking difference is that light is focused by the drop. With a judicious placement of a detector directly behind the drop, only light focused by the drop is detected. While this is a potentially useful system for measuring very turbid samples, focusing light that is scattered seems at first hardly an advantage since agglutination generally results in more light being scattered in the forward direction. Detecting an effective change in agglutination would seem to warrant having the largest change between isotropic scattering with individual particles and attenuated forward scattering with large clusters.

However, a simple analysis illustrated in FIG. 12 based on classical optics suggests that the drop geometry does provide an advantage. If a small object with a circular projection of area $A_S$ blocks light perfectly in the path of light moving through the cuvette to the detector, then the measured intensity (I1) at the detector of area $A_D$ is simply:

$$\frac{I_1}{I_o} = 1 - \frac{A_S}{A_D}$$

However, assuming a simple model of the drop focusing such that the light rays are together conical in shape, the intensity of light reaching the detector depends on the location of the object.

$$\frac{I_1}{I_o} = \left(\frac{1}{1-\frac{x}{L}}\right)^2 \left[1 - \frac{A_S}{A_D}\left(\frac{1}{1-\frac{x_s}{L}}\right)^2\right]$$

The relevant conclusion of this analysis is a comparison between the response of the drop versus the cuvette as the size of the object changes with time and hence "blocks" more light. The ratio of the two responses is simply:

$$\frac{\text{Drop intensity change}}{\text{Cuvette intensity change}} = \left(\frac{1}{1-\frac{x_s}{L}}\right)^2$$

where $x_s$ is the position of the object from the base (x=0) to the detector (x<L) assuming that the detection window area is the same for both. In essence, focusing the light forces a greater difference if the object is present along the axis of the drop and especially towards the side where the cone of light is most narrow due to focusing of the rays.

As a first test of the drop system, to a suspension of 1 micrometer diameter particles a one thousand-fold lower concentration of 2 micrometer diameter particles was added. In FIG. 12 the signal increase with a cuvette for this mixture was effectively zero (less than 1%) for all wavelength ranges, whereas using the drop the signal increase was nearly 20%, with the greatest change over the 400-480 nm. It is important to note that there is a significant difference in the attenuation of scattering in the forward direction in this size range with the signal increasing upon addition of the 2 micrometer diameter particles and that shorter wavelengths accentuate the difference. This is expected since Rayleigh theory shows that scattering depends upon the fourth power of the wavelength of light.

With the basic proof of concept in hand, we set out to conduct an agglutination immunoassay using human serum samples and a commercially available particle immunoassay kit for detecting C Reactive Protein. Also tested was a low cost prototype instrument built using near infrared diodes and an operational amplifier to boost the signal (FIG. 3). For both systems, after a few seconds and through a period of 2 minutes the human serum samples that contained a level of C Reactive Protein above a clinically significant level of 6 ng/ml had a change in signal whose rate was measured to be −0.15+/−0.02/min for the fiber optic based spectrometer system and −0.19+/−0.05/min for the low cost prototype system. For both instruments, negative human serum and various buffer solutions were found to have very small changes in light in this time range and were easily identified as "negative". Both instruments were able to distinguish between human serum containing more than 6 ng/ml of C Reactive Protein within 2 minutes by specific antibody detection of C Reactive Protein.

Figure 13:
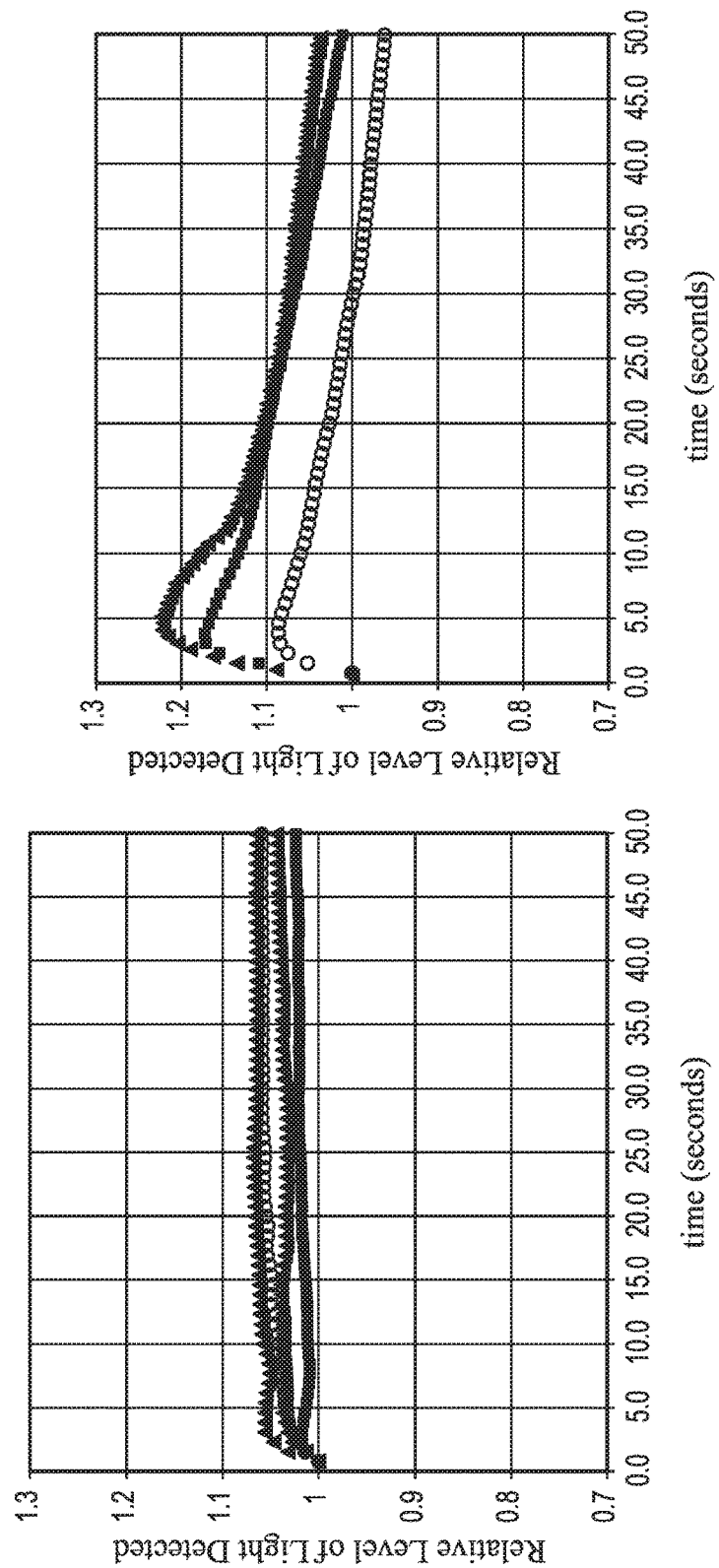
FIG. 13 Rate data from the fiber optic system for negative human serum and buffer solution is shown on the left hand side and there is essentially no change in signal over 50 seconds. For the graph on the right-hand side the positive human serum samples have a rapid increase in signal followed by a slower decrease in signal.

In FIG. 13, a detailed time-series of light detected with the positive human serum samples for the fiber optic based spectrometer shows that shortly after the drops are combined, the signal reaches a maximum very quickly before slowly dropping at an essentially constant rate. This is not caused by mixing since this dramatic change is not observed with the negative samples, and the inventors believe that the following explains this behavior. In the presence of C Reactive Protein concentrations at higher than the clinically significant threshold value, the particle concentration of the immunoassay is sufficient to form a network of particles in an essentially irreversible aggregation process which at short times is dominated by doublet formation. In this stage of the process the total particle concentration decreases nonlinearly in a multi-stage reaction that depends upon both particle containing antibodies and C Reactive protein concentrations. It is presumed that binary collisions predominate, although the high particle concentrations used may include three body collisions. Binary collisions lead to a rapid drop in the number of scattering particles without a significant change in the scattering efficiency. This is a reasonable assumption based on simple physical arguments that tightly agglutinated pairs decrease the effective cross section of scattering as compared to freely diffusing single particles. Using Monte Carlo simulation based on the assay conditions and comparing a suspension of 140 nm particles (the nominal diameter particles used in the assay) versus 280 nm particles at half the concentration shows a reduction in transmitted light for a planar, unfocused light source. Addition of a correction factor due to the geometry of two spheres vs. one large sphere accentuates this result.

For longer times (e.g. after 10-15 seconds), the agglutination reaction is dominated by thermal motion and the total particle concentration decreases less rapidly and asymptotically approaches a value dictated by the aggregate size that grows slower due to the reduction of the aggregate diffusivity. For a given initial particle concentration, the concentration of the antigen dictates the speed at which the growing aggregates reach this self-limiting size for further growth. The effect on the focused light intensity in this regime becomes dominated by the higher light scattering by the larger particle aggregates. Combining these two effects leads to the transmitted light decreasing relatively linearly with time.

Two concluding remarks may be helpful in order to assess how this technique relates to existing instrumentation for detecting particle aggregation, especially in immunoassays. First, the light focused by the drop is best considered to form caustics rather than what is usually the case in the employment of lenses where a sharp focus is desired. Caustics unlike the sharp focus obtained using commercial lenses, have two important qualities. The first is genericity; which Bruce and colleagues [8] define for caustics as "in spirit, meaning 'not behaving in an unnecessarily special way.'" More rigorously, this means that in order to be called generic, a caustic must have the properties: (1) be able to be approximated arbitrarily closely by a generic one; and (2) that every caustic sufficiently close to a generic one is also generic [8]. The lenses used to create a point of sharp focus are non-generic, as it is extremely remote that a generic lens would produce the focus. However, a water drop on a superhydrophobic surface (such as a raindrop on a plant leaf, or the sample droplet used in this device) will always produce a caustic with regions of localized high intensity. The second quality of a caustic is its structural stability, which means that a caustic maintains its identity even when perturbed [9-10]. With a water drop placed on a superhydrophobic surface, if the drop is moved slightly, has a slightly different volume (due to lack of precision with the pipetter), or has a slightly differently shape (due to inhomogeneities on the superhydrophobic surface), it will still produce a caustic with local regions of high light intensity. This cusp of high intensity will be relatively insensitive to small perturbations of the drop position, size, or shape. Thus, this drop device will be rather forgiving to these perturbations, whereas a spherical container using paraxial rays to project a sharp geometrical focus onto the detector widow would be very unforgiving, and to make such a device work better than a simple cuvette, it would need to have a means to hold the spherical "cuvette", light source, and detector in a very precise position.

A second remark worthy of mention is that at least one commercially available nephelometer [11] employs a lens system to focus light scattered at a very small angle from a cuvette. The advantage of this approach appears to be in the ability to detect a wider range of agglutination. Similarly, the method described here is believed to work well for samples of a wide range of particle concentration, but there is an added benefit of particle mobility. Individual particles move towards the surface of the drop while aggregates accumulate towards the center, adding to the ability of the drop system to detect changes in forward scattering rapidly and at high particle concentrations.

Methods

Superhydrophobic Surfaces

Commercial-grade LDPE sheet, 1.59 mm (1/16 inch) thick was purchased from McMaster-Carr (Santa Fe Springs, Calif.). The materials used to grow the crystals were LDPE pellets (Sigma-Aldrich, St. Louis, Mo.) with a melt index of 2.50 g/min at 190° C., xylene(isomers plus ethylbenzene, reagent grade, Sigma-Aldrich), and methyl ethyl ketone (reagent grade, J. T. Baker, Phillipsburg, N.J.). The LDPE sheet was cut into 61×99 mm (2.40×3.90 in) rectangles, lightly abraded, and cleaned with acetone. The LDPE pellets and chemicals were used without additional preparation.

The experimental procedure involved placing the xylene and LDPE pellets in a boiling flask held at 92±2° C. After the LDPE had fully dissolved (approximately 45 min), the MEK was added to the flask. The addition of the nonsolvent to the solvent-plastic solution was shown by Erbil and colleagues (2003) to increase surface roughness and aqueous drop contact angle for solvent-cast polypropylene. After the turbidity caused by the MEK addition cleared, the bath was reduced to 87±2° C. After the desired period of heat soak time had elapsed, 5.25 mL of solution were pipetted onto the surface in the solvent-casting fixtures. This volume corresponded to approximately 0.1 mL of solution per cm2 of substrate. The fixtures were placed under overturned deep crystallizing dishes (as slower evaporation promoted better crystal growth) and left in a fume hood to dry at room temperature.

Fiber Optic Spectrometer Detector

The heart of this system is the spectrometer (model USB2000 Miniature Fiber Optic Spectrometer, Ocean Optics). This spectrometer accepts incident radiation transmitted through a single-strand optical fiber (400 µm fiber diameter, UV-vis [200-1100 nm] Laboratory-grade Patch Cord Optical Fiber Assembly, Ocean Optics) and disperses it via a fixed grating across the 2048-element linear CCD array detector. The operating software (SpectraSuite, v.

2.0.109, Ocean Optics) runs on a Power Mac G4 (Apple, Cupertino, Calif.). An achromatic collimating lens (350-2000 nm) (model 74-ACR, Ocean Optics) was used to collect the incident light to the optical fiber.

Several custom parts were fabricated or purchased and integrated into the Ocean Optics system. First, a light source was needed. As it was not known a priori what wavelength would best measure the agglutination of the custom immunoassay, a broadband continuous visible light source was chosen. It was desired to choose a source that had minimal drift and emitted minimal heat that might affect results by increasing the evaporation of aqueous samples. For these reasons, a high-power white LED (LUXEON I emitter, p/n LXHL-BW02, Philips Lumileds, San Jose, Calif.) was chosen. This is a neutral white, 1 W high power (45 lm typ.) LED. The "batwing" emitter style was chosen, as this has a constant intensity over ±15° from the axis. A line-voltage input dedicated LED power supply (350 mA i-Xitanium, Advance Transformer, Rosemont, Ill.) was used to drive the LED with minimal drift and fluctuation. In addition, as LED intensity is a function of junction temperate, a large aluminum heat sink was used to maintain the LED at ambient room temperature.

To maintain alignment yet allow adjustment on individual axes, a custom fixture was assembled to hold all the parts other than the spectrometer, cables, and computer. A 19 mm thick acrylic plate was machined to rigidly attach the power supply, power switch, fiber optic cable bracket (a modified 4-way Cuvette Holder for 1-cm Cuvettes, p/n CUV-ALL-UV, Ocean Optics), and fixed U-channel for the LED.

A sliding inner tray was made to hold the LED, which slid inside the outer fixed U-shaped channel. In this way the LED distance from the fiber optic collection cable could be varied. A fixed ruler gave means to position the LED in a repeatable fashion. Unlike with a cuvette, it was felt that the vertical positioning of the drop with respect to the fiber optic cable would be important. Therefore, a custom z-direction stage was machined and incorporated into the Ocean Optics 4-way Cuvette Holder. This consisted of a custom translating platform using a micrometer head (model 261M, L. S. Starrett Co., Athol, Mass.).

Additional custom parts were machined in the quest to optimize the output signal. These parts included a dummy collimating lens barrel, which was used to determine if a better signal was achieved with or without the collimating lens (while maintaining the position of the fiber optic cable with respect to the sample). As further use of the spectrometer setup demonstrated the focusing effect of using a drop of sample, it was desired to investigate the effect of using smaller apertures to increase the s/n ratio of the signal. Therefore, a set of custom apertures was fabricated using 0.12 mm thick brass sheet, with apertures of 1.25, 1.75, 2.0, and 2.75 mm diameter).

To minimize positioning errors caused by manually holding the pipette used to deposit the reagent and analyte on the superhydrophobic surface, the pipette was rigidly clamped in a holding fixture with the tip a small distance above the analyte drop (but out of the light path). This was accomplished by fixing a handscrew (Jorgensen No. 4, Adjustable Clamp Co., Chicago, Ill.) at the appropriate height, and then clamping the pipette in the handscrew. This way, the drop could be placed at the desired x-y position after the analyte drop had been dispensed on the sample surface, and this fixture used to deposit the reagent without affecting the position of the drop.

Particles and Assay

Light transmission through a suspension of 1 micron carboxylated polystyrene divinylbenze particles (Polysciences Inc.) at a concentration of 10 µg/mL in DI water was measured using a cuvette and a drop on a superhydrophobic surface. To simulate agglutination, to the above solution 10 ng/mL of 2 µm particles was added. The results obtained using a drop (40 µL of either the control or the "spiked" solution) and a cuvette (500 µL of either the control or the "spiked" solution) were compared. For these comparative runs, the same aperture (2 mm) and LED position were used. The drop had a maximum pathlength of approximately 4.4 mm, and the cuvette 10 mm. To achieve a good signal, the integration time was doubled (to 100 ms) for the cuvette.

The Cen-Med Sure-Vue CRP assay (Biokit S.A., Barcelona Spain; distributed by Fisher) is a card-based assay for clinical use. The latex reagent consists of an approximately 0.2% w/v suspension, in buffer, of 140 nm nominal size latex polystyrene particles coated with rabbit anti-human IgG for CRP. The positive control is diluted human serum containing more than 6 mg/L of CRP, and the negative control is diluted human serum containing less than 6 mg/L of CRP. In addition to the negative control supplied with the kit, other negative controls were tested as well on the forward-scattering nephelometer, to eliminate the possibility that other effects could account for the strong signal increase seen when the positive control was used as the analyte. These negative controls comprised 0.9% NaCl (the buffer recommended by the kit directions as a dilution buffer for semi-quantitative testing); BSA 50 g/L in 100 mM phosphate buffer (simulating the total protein concentration in serum); and unconjugated (as-supplied), carboxylated 2 µm and 3 µm particles (Polysciences Inc., Warrington, Pa.) in 0.9% NaCl.

References for Example 4

[1] Gao L and McCarthy T J (2000) Artificial Lotus Leaf Prepared Using a 1945 Patent and a Commercial Textile. Langmuir 22:5998-6000

[2] Rastogi V et al. (2008) Synthesis of Light-Diffracting Assemblies from Microspheres and Nanoparticles in Droplets on a Superhydrophobic Surface. Adv Materials 20(22): 4263-4208

[3] Posthuma-Trumpie, G., Korf J., and Van Amerongen A., "Lateral flow (immuno)assay: its strengths, weaknesses, opportunities and threats. A literature survey" Analytical and Bioanalytical Chemistry, Volume 393, Number 2, 570-582 (2009).

[4] Erbil H Y et al. (2003) Transformation of a Simple Plastic into a Superhydrophobic Surface. Science 299: 1377-1380

[5] Schneider J, Egatz-Gomez A et al. (2008a) Motion of viscous drops on superhydrophobic surfaces due to magnetic gradients. Colloids and Surfaces A: Physicochemical and Engineering Aspects 323(1-3):19-27

[6] Rastogi V et al. (2010) Anisotropic Particle Synthesis Inside Droplet Templates on Superhydrophobic Surfaces. Macromol. Rapid Comm 31(2): 190-195

[7] Egri A, Horvath A. Kirska G., Horvath G. (2010) Optics of sunlit water drops on leaves: conditions under which sunburn is possible. New Phytologist 185(4):979-987

[8] Bruce J W, Giblin P J, Gibson C G (1984) Caustics through the looking glass. The Mathematical Intelligencer 6(1): 47-58

[9] Nye J F (1999) Natural focusing and the fine structure of light: Caustics and wave dislocations. Bristol, UK: Institute of Physics Publishing.

[10] Marston, P. L., Kaduchak, Generalized rainbows and unfolded glories of oblate drops: organization for multiple internal reflections and extension of cusps into Alexander's dark band, Applied Optics Vol. 33 (21) July 1995 4702-4713

[11] Desjarlais F., Daigueault, "Basic Characteristics and Evaluation of a Partially Automated Behring Laser Nephelometer for the Measurement of IgG, IgA Clin. Biochem. 14 (2) 51-56 (1981).

What is claimed is:

1. A method for determining the presence of a protein in an aqueous liquid biological sample, comprising:
    a. depositing a droplet of the aqueous liquid biological sample on a surface consisting of a superhydrophobic material, wherein all portions of the surface are superhydrophobic, that is thermodynamically incompatible with the bulk liquid of the aqueous liquid sample, wherein said droplet forms a liquid lens having a contact angle with the superhydrophobic surface of no less than about 150°;
    b. depositing nanoparticles onto the surface of the droplet of the aqueous liquid biological sample, wherein said nanoparticles are capable of aggregating in the presence of said protein;
    c. exposing the liquid lens to focused light from a light source in parallel with a surface of said lens; and
    d. measuring a time-dependent change in intensity of the focused light, relative to an initial intensity;
    wherein a change in light intensity indicates the presence of said protein.

2. The method of claim 1, wherein said nanoparticles are selected from the group consisting of gold, silver and latex nanoparticles.

3. The method of claim 1, wherein said nanoparticles have a diameter of between about 20 nm and about 300 nm.

4. The method of claim 1, wherein said nanoparticles are silver nanoparticles having a diameter of about 20 nm.

5. The method of claim 1, wherein said intensity of the light is measured for a period of about 10 seconds to about 30 seconds.

6. The method of claim 1, wherein the aqueous liquid biological sample is blood, plasma, serum, gastrointestinal secretions, homogenates of tissues or tumors, synovial fluid, feces, urine, saliva, sputum, cyst fluid, amniotic fluid, cerebrospinal fluid, peritoneal fluid, lung lavage fluid, semen, lymphatic fluid, tears, prostatic fluid, or a combination thereof.

7. The method of claim 1, wherein the superhydrophobic surface is coated with a material selected from the group consisting of silicone compounds, silanes, fluorocarbon polymers, perfluoroalkyl ethyl methacrylate (PPFEMA) coated polycaprolactone, hydrocarbons, polymer mats made of polystyrene and poly[tetrafluoroethylene-co-(vinylidene fluoride)-co-propylene] (PTVFP), polyethylene glycol with glucose and sucrose in conjunction with a superhydrophobic substance, combinations of nanoparticles with polyethylene or polypropylene; high density polyethylene, technical waxes, films of rough particles of metal oxides, polymer binder layers containing a plurality of porous protrusions, and a combination thereof.

8. The method of claim 1, wherein the light source is a source of UV light, visual light, NIR light, IR light, or a combination thereof.

9. The method of claim 1, wherein said superhydrophobic surface comprises a hold, defect, post, or depression in order to rigidly hold the aqueous liquid sample in place.

10. The method of claim 1, wherein the light source is a light emitting diode (LED).

11. The method of claim 1, further comprising positioning a detector at a focal point colinear to the light source.

12. The method of claim 1, wherein the presence of said protein is detected when:
    i) the measured time-dependant change in intensity is a time-dependant increase in intensity, relative to the initial intensity, where the initial intensity is measured when the nanoparticles are deposited onto the surface of the droplet; or
    ii) the measured time-dependant change in intensity is a time-dependant decrease in intensity, relative to the initial intensity, where the initial intensity is measured a few seconds after the nanoparticles are deposited onto the surface of the droplet.

13. A method for determining the presence of a protein in an organic solvent, comprising:
    a. depositing the organic solvent on a superoleophobic surface, wherein all portions of the superoleophobic surface are thermodynamically incompatible with the bulk liquid of the organic solvent, wherein said organic solvent forms a liquid lens having a static organic solvent contact angle with the superoleophobic surface of more than about 120°;
    b. depositing a drop of nanoparticles onto the surface of the organic solvent, wherein said nanoparticles are capable of aggregating in the presence of said protein;
    c. exposing the liquid lens to focused light from a light source in parallel with the surface of said lens; and
    d. measuring a time-dependent change in intensity of the focused light, relative to an initial intensity;
    wherein a change in light intensity indicates the presence of said protein.

14. A method for determining the presence of an analyte in a liquid biological sample, comprising:
    a. contacting the liquid biological sample with a binding substance specific to the analyte sought to be determined, said binding substance being immobilized on a nanoparticle or microparticle;
    b. depositing the liquid biological sample with the binding substance on a surface that is thermodynamically incompatible with the bulk liquid of the biological sample wherein said liquid biological sample forms a bead having a contact angle with the thermodynamically incompatible surface of no less than about 150°;
    c. exposing the liquid biological sample with the binding substance to focused light from a light source in parallel with the surface; and
    d. measuring a time-dependent change in light intensity, relative to an initial intensity, wherein a change in light intensity indicates the presence of the analyte,
    wherein all portions of the surface are thermodynamically incompatible with the bulk liquid of the biological sample.

15. The method of claim 14, wherein said nanoparticle or microparticle has a known size or size distribution.

16. The method of claim 14, wherein the surface is superhydrophobic.

17. The method of claim 14, wherein the liquid biological sample is aqueous.

18. The method of claim 14, wherein the liquid biological sample is blood, plasma, serum, gastrointestinal secretions, homogenates of tissues or tumors, synovial fluid, feces, urine, saliva, sputum, cyst fluid, amniotic fluid, cerebrospinal fluid, peritoneal fluid, lung lavage fluid, semen, lymphatic fluid, tears, prostatic fluid, or a combination thereof.

19. The method of claim 14, wherein the binding substance is an antibody specific against the analyte.

20. The method of claim 19, wherein the antibody is a monoclonal antibody.

21. The method of claim 14, wherein the binding substance is a ligand specific against the analyte.

22. The method of claim 14, wherein the binding substance is a polynucleotide specific against the analyte.

23. The method of claim 14, wherein the surface is coated with a material selected from the group consisting of silicone compounds, silanes, fluorocarbon polymers, perfluoroalkyl ethyl methacrylate (PPFEMA) coated polycaprolactone, hydrocarbons, polymer mats made of polystyrene and poly[tetrafluoroethylene-co-(vinylidene fluoride)-co-propylene] (PTVFP), polyethylene glycol with glucose and sucrose in conjunction with a hydrophobic substance, combinations of nanoparticles with polyethylene or polypropylene; high density polyethylene, technical waxes, films of rough particles of metal oxides, polymer binder layers containing a plurality of porous protrusions, and combinations thereof.

24. The method of claim 14, wherein the surface is a metallo-organic compound, metal, treated glass, clay or a combination thereof.

25. The method of claim 14, wherein the light source is a source of UV light, visual light, NIR light, IR light, or a combination thereof.

26. The method of claim 25, wherein the wavelength is about the same diameter as the nanoparticle or microparticle.

27. The method of claim 14, wherein the step of measuring the change in light intensity further comprises measuring an increase in forward light scatter, relative to an initial light scatter, as a function of time; and
wherein the step of measuring the increase in forward light scatter is preceded by a step of depositing another portion of the same liquid biological sample on the thermodynamically incompatible surface with the same nanoparticle or microparticle in the absence of the binding substance.

28. The method of claim 27, wherein the step of measuring the increase in forward light scatter as a function of time comprises comparing the changes in light scattering between said liquid biological sample contacted with said binding substance and said another portion of the same liquid biological sample.

29. The method of claim 14, wherein:
the liquid biological sample comprises a bodily fluid or a tissue sample from a patient;
the analyte is characteristic of an infectious disease; and
said change in light intensity indicates the presence of the infectious disease in the patient.

30. The method of claim 14, wherein the light source is a light emitting diode (LED).

31. The method of claim 14, further comprising positioning a detector at a focal point colinear to the light source.

* * * * *